US008696917B2

(12) United States Patent  
Petisce et al.

(10) Patent No.: US 8,696,917 B2  
(45) Date of Patent: Apr. 15, 2014

(54) ANALYTE SENSOR AND FABRICATION METHODS

(75) Inventors: James R. Petisce, San Clemente, CA (US); David Zhou, Santa Clarita, CA (US); Mena Valiket, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 726 days.

(21) Appl. No.: 12/699,302

(22) Filed: Feb. 3, 2010

(65) Prior Publication Data

US 2010/0200538 A1 Aug. 12, 2010

Related U.S. Application Data

(60) Provisional application No. 61/151,136, filed on Feb. 9, 2009.

(51) Int. Cl.
*H01B 13/00* (2006.01)

(52) U.S. Cl.
USPC ............... 216/13; 216/17; 216/20; 216/36; 600/347

(58) Field of Classification Search
USPC .................. 216/13, 17, 20, 36; 600/347
See application file for complete search history.

(56) References Cited

U.S. PATENT DOCUMENTS

| 5,108,819 A | 4/1992 | Heller et al. |
| 5,391,250 A | 2/1995 | Cheney, II et al. |
| 5,568,806 A | 10/1996 | Cheney, II et al. |
| 7,781,047 B2 * | 8/2010 | Majumdar et al. ......... 428/195.1 |
| 2004/0133164 A1 * | 7/2004 | Funderburk et al. .......... 604/134 |
| 2005/0054909 A1 * | 3/2005 | Petisce et al. ................. 600/345 |
| 2007/0227907 A1 * | 10/2007 | Shah et al. ................. 205/777.5 |
| 2008/0131315 A1 | 6/2008 | Takase et al. |
| 2010/0118243 A1 * | 5/2010 | Majumdar et al. ............ 349/122 |
| 2010/0219071 A1 * | 9/2010 | Bhullar et al. .......... 204/403.01 |

FOREIGN PATENT DOCUMENTS

| EP | 0276979 A2 | 8/1988 |
| EP | 1288653 A1 | 3/2003 |
| EP | 1360933 A | 12/2003 |
| WO | 0250534 A | 6/2002 |
| WO | 2006063063 A | 6/2006 |
| WO | 2007070093 A2 | 6/2007 |

OTHER PUBLICATIONS

International Search Report, Dec. 3, 2010.
Supplementary European Search Report, Apr. 19, 2013.
Japanese Office Action, Jun. 7, 2013.
Chinese Office Action, Jul. 10, 2013.

* cited by examiner

*Primary Examiner* — Binh X Tran
(74) *Attorney, Agent, or Firm* — Michael Crapenhoft

(57) ABSTRACT

Methods for fabricating analyte sensor components using IC- or MEMs-based fabrication techniques and sensors prepared therefrom. Fabrication of the analyte sensor component comprises providing an inorganic substrate having deposited thereon a release layer, a first flexible dielectric layer and a second flexible dielectric layer insulating there between electrodes, contact pads and traces connecting the electrodes and the contact pads of a plurality of sensors. Openings are provided in one of the dielectric layers over one or more of the electrodes to receive an analyte sensing membrane for the detection of an analyte of interest and for electrical connection with external electronics. The plurality of fabricated sensor components are lifted off the inorganic substrate.

8 Claims, 14 Drawing Sheets

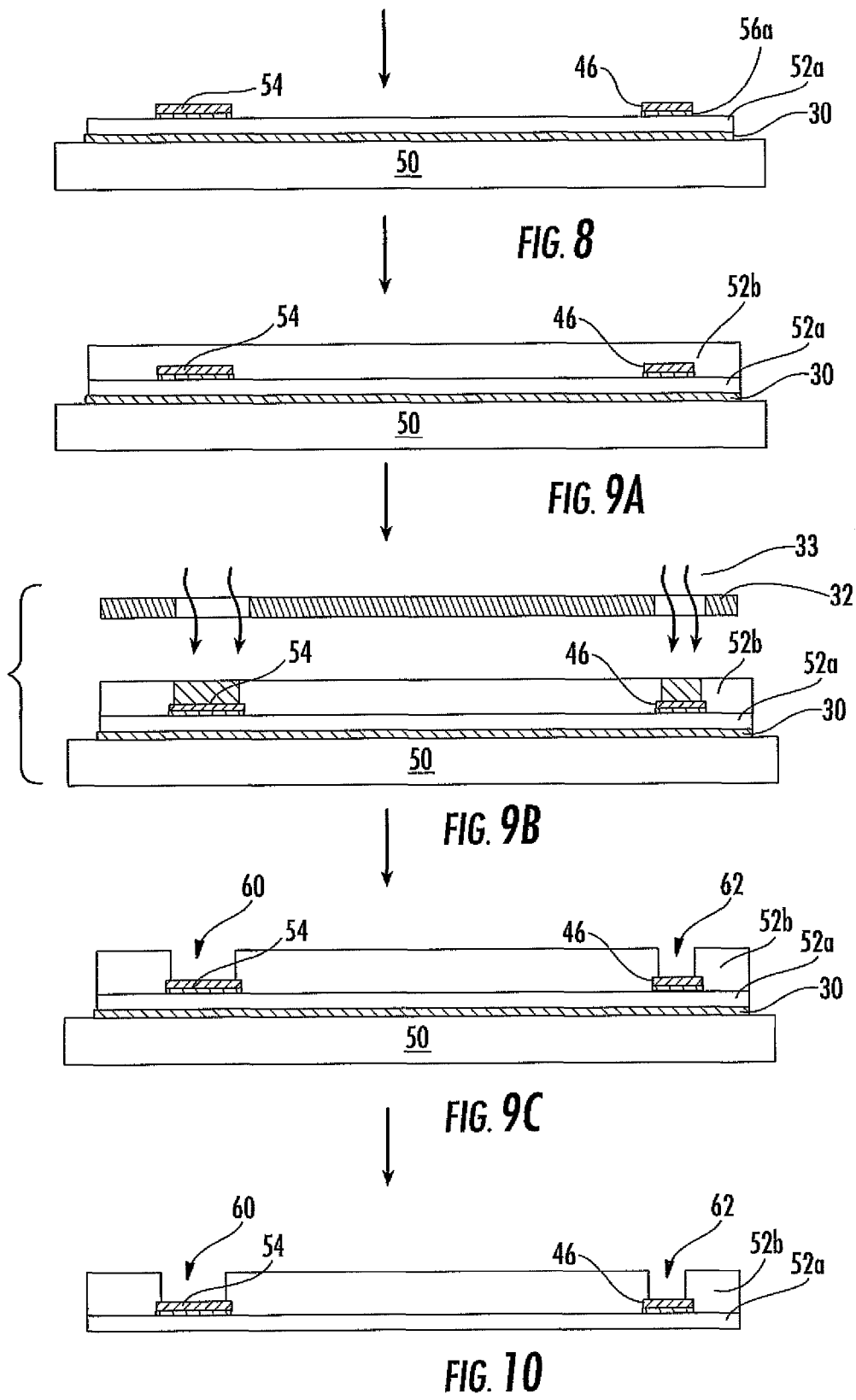

ANALYTE SENSOR AND FABRICATION METHODS

CROSS-REFERENCE TO RELATED APPLICATIONS

This application claims the benefit of U.S. Provisional Application No. 61/151,136, filed Feb. 9, 2009, which is hereby incorporated by reference in its entirety.

BACKGROUND

1. Field of the Invention

The invention relates generally to analyte measuring systems and methods, and more particularly to methods for manufacturing of analyte sensors using microfabrication and lift-off techniques.

Controlling blood glucose levels for diabetics and other patients can be a vital component in critical care, particularly in an intensive care unit (ICU), operating room (OR), or emergency room (ER) setting where time and accuracy are essential. Presently, one of the most reliable ways to obtain a highly accurate blood glucose measurement from a patient is by a direct time-point method, which is an invasive method that involves drawing a blood sample and sending it off for laboratory analysis. This time-consuming method is often incapable of producing needed results in a timely manner. Other minimally invasive methods such as finger-stick methods involve the use of a lancet or pin to pierce the skin to obtain a small sample of blood, which is then applied to a test strip and analyzed by a glucose meter. While these minimally invasive methods may be effective in determining trends in blood glucose concentration, they generally do not track glucose accurately enough to be used for intensive insulin therapy, for example, where inaccuracy at conditions of hypoglycemia could pose a very high risk to the patient.

Electrochemical analyte sensors have been developed for measuring various analytes in a substance, such as glucose. An analyte is a substance or chemical constituent that is determined in an analytical procedure, such as a titration. For instance, in an immunoassay, the analyte may be the ligand or the binder, where in blood glucose testing, the analyte is glucose. Electro-chemical analyte sensors comprise electrolytic cells including electrodes used to measure an analyte. Two types of electrochemical analyte sensors are potentiometric and amperometric analyte sensors.

Amperometric analyte sensors, for example, are known in the medical industry for analyzing blood chemistry. These types of sensors contain enzyme electrodes, which typically include an oxidase enzyme, such as glucose oxidase, that is immobilized behind a membrane on the surface of an electrode. In the presence of blood, the membrane selectively passes an analyte of interest, e.g. glucose, to the oxidase enzyme where it undergoes oxidation or reduction, e.g. the reduction of oxygen to hydrogen peroxide. Amperometric analyte sensors function by producing an electric current when a potential sufficient to sustain the reaction is applied between two electrodes in the presence of the reactants. For example, in the reaction of glucose and glucose oxidase, the hydrogen peroxide reaction product may be subsequently oxidized by electron transfer to an electrode. The resulting flow of electrical current in the electrode is indicative of the concentration of the analyte of interest.

Manufacture of analyte sensor can be problematic. To achieve accurate analyte measurement, close tolerances must be achieved during manufacture. For example, slight differences in the dimensions of the first and second working electrodes can create an electrical offset between the outputs of the two electrodes. This offset may result in a less accurate analyte concentration measurement. Many analyte manufacturing techniques require a large number of steps, where each step may introduce error and/or tolerance variations. This, in turn, results in difficulty in manufacturing of large numbers of analyte sensors with high reliability and repeatability.

SUMMARY

Aspects of the present invention provide for the manufacture of miniaturized biosensors components and methods for measuring an analyte concentration using an analyte sensor, which can be further miniaturized. The systems and method include an analyte sensor manufactured using microelectromechanical (MEMs) and/or integrated circuit (IC) fabrication processes. The resultant analyte sensor is capable of sensing the analyte concentration and outputting a signal corresponding to the analyte concentration. With the disclosed aspects, the number of production steps of the assembly of functional in vivo sensors can be reduced. Accordingly, mass produced, high density, cost reduced, high reliability sensors will be achieved.

MEMs and/or IC fabrication technology provides for the manufacture of amperometric sensor components suitable for analyte detection, and in particular, glucose detection. MEMs and/or IC fabrication technology makes possible analyte sensor components of sub-micron to micron size that can be integrated with other electronics. Furthermore, MEMs and/or IC fabrication technology provides for batch fabrication of analyte sensors in large quantities, thus reducing costs while potentially improving quality. MEMs/IC sensors are fabricated through batch production process employing lithography, which provides 3-dimensional structures using pre-designed resist patterns (masks). Applicants have determined that amperometric analyte sensor manufacturing may be advantageously integrated into MEMs/IC fabrication technology to provide accurate, high quality sensors for detection of analytes of interest.

According to one aspect of the present invention, methods are provided for MEMs and/or IC fabrication of an analyte sensor component. An analyte sensor component is fabricated on a semiconductor substrate and comprises at least one of continuously connected isolated reference, working, and blank electrode.

In a first embodiment, a method for fabricating an electrochemical sensor component is provided. The method comprises providing an inorganic substrate, depositing a release layer on substantially all of the substrate, depositing a first flexible dielectric layer on substantially all of the release layer, and isolating, between a first flexible dielectric layer and a second flexible dielectric layer, a plurality of individual continuously connected electrodes, traces and contact pads comprised of a conductive material. Forming openings in the second flexible dielectric layer exposing at least a portion of at least one of the individual continuously connected electrodes and contact pads, and separating the electrochemical sensor component from the inorganic substrate.

In one aspect of the first embodiment, the release layer comprises (i) a solubility in a solvent that does not dissolve the first or second flexible dielectric layers; (ii) an etch rate (wet or dry) faster than the first flexible dielectric layer; or (iii) a pressure sensitive adhesive material interposed between the first dielectric material and the inorganic substrate.

In other aspect of the first embodiment, the method further comprises depositing an analyte sensing membrane in the opening over the electrode of the electrochemical sensor component.

In a second embodiment, a method for fabricating an electrochemical sensor component is provided. The method comprises (i) providing an inorganic substrate, (ii) depositing a release layer on the inorganic substrate, (iii) depositing a first flexible dielectric layer on the release layer, (iv) defining perimeters in the first flexible dielectric layer of a plurality of individual continuously connected electrodes, traces and contact pads, (v) depositing conductive material in at least a portion of the perimeters formed in the first flexible dielectric layer, (vi) depositing a second flexible dielectric layer over the plurality of individual continuously connected electrodes, traces and contact pads and the first flexible dielectric layer, and (vii) forming openings in the second flexible dielectric layer exposing at least a portion of at least one of the individual continuously connected electrode and contact pad, and (ix) chemically separating the first electrochemical sensor component from the inorganic substrate.

In one aspect of the second embodiment, the release layer comprises (i) a solubility in a solvent that does not dissolve the first or second flexible dielectric layers; (ii) an etch rate (wet or dry) faster than the first flexible dielectric layer; or (iii) a pressure sensitive adhesive material interposed between substantially all of the first dielectric material and the inorganic substrate.

In another aspect of the second embodiment, the method further comprises depositing an analyte sensing membrane in the opening over the electrode.

In a third embodiment, a method for fabricating an electrochemical sensor component is provided. The method comprises (i) providing an inorganic substrate, (ii) depositing a release layer on the inorganic substrate, (iii) depositing a first flexible dielectric layer on the release layer, (iv) depositing conductive material on the first flexible dielectric material, (v) depositing a mask layer on the conductive material, (vi) defining perimeters for at least one continuously connected electrode, trace and contact pad in the mask layer, (vii) forming a plurality of individual continuously connected electrodes, traces and contact pads of the conductive material as defined by the perimeters in the mask layer, (viii) depositing a second flexible dielectric layer over the plurality of individual continuously connected electrodes, traces and contact pads and the first flexible dielectric layer, (ix) forming at least one opening in the second flexible dielectric layer exposing at least a portion of at least one of the individual continuously connected electrodes and contact pads, and (x) chemically separating the electrochemical sensor component from the substrate.

In one aspect of the third embodiment, the release layer comprises (i) a solubility in a solvent that does not dissolve the first or second flexible dielectric layers; (ii) an etch rate (wet or dry) faster than the first flexible dielectric layer; or (iii) a pressure sensitive adhesive material interposed between substantially all of the first dielectric material and the inorganic substrate.

In another aspect of the third embodiment, the method further comprises depositing an analyte sensing membrane in the opening over the electrode.

An electrochemical analyte sensor made by the methods described herein is also provided.

BRIEF DESCRIPTION OF THE DRAWINGS

Henceforth reference is made the accompanied drawings and its related text, wherein:

FIG. 5-10 are schematic diagrams of a cross-sectional views illustrating the first embodiment of a fabrication process of an electrochemical sensor component;

DETAILED DESCRIPTION

Figure 1:
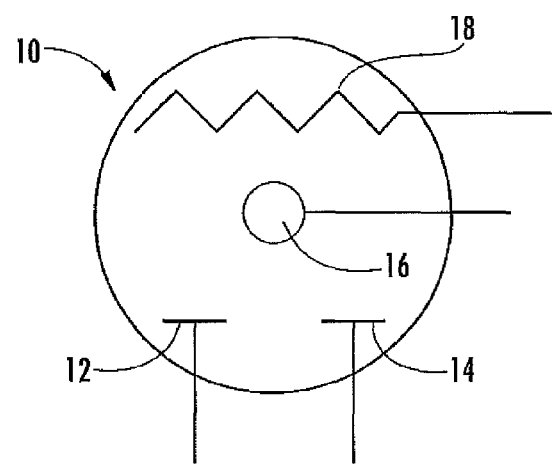
FIG. 1 is a schematic diagram of a four-electrode electrochemical sensor component used in some aspects of the present invention.

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Disclosed are methods for fabricating analyte sensors, such as a glucose sensor, using IC- or MEMS-based fabrication techniques. Fabrication of the analyte sensor comprises providing an inorganic substrate, isolating, between a first flexible dielectric layer and a second flexible dielectric layer, a plurality of individual continuously connected electrodes, traces and contact pads comprised of a conductive material, where the first flexible dielectric layer is deposited on the inorganic substrate, and forming openings in the second flexible dielectric layer exposing at least a portion of one of the individual continuously connected electrodes and contact pads. Openings are provided to receive an analyte sensing membrane for the detection of an analyte of interest and for electrical connection with the contact pads. In one aspect, the fabricated sensor component may be lifted off the semiconductor substrate and incorporated into a flex circuit or medical device.

The inorganic substrate may be a semiconductor. Suitable semiconductor substrates may be of conventional semiconductor materials such as silicon, silicon dioxide, or gallium arsenide. Silicon substrates may have native oxide or polysilicon layer or may have silicon nitride layers. Other inorganic, semi-conductive or non-conductive materials may be used as a substrate. In one aspect, the inorganic substrate excludes borosilicate glasses as these materials are generally not readily adaptable to MEMs/IC processing.

In one aspect, fabrication of the analyte sensor comprises depositing a release layer on the substrate to provide for subsequent release of the fabricated sensor component. In this aspect, a plurality of fabricated sensor components may be "lifted off" the substrate, providing for sensors with sufficient flexibility for incorporation into or on flex circuits, medical devices, e.g., catheters, and the like.

In a preferred aspect, the release layer preferably has one or more of the following attributes: a solubility in a solvent that does not dissolve subsequently formed flexible dielectric layers; etches (wet or dry) at a rate faster than that of the first flexible dielectric layers of the sensor; or is a pressure sensitive adhesive material interposed between substantially all of the first dielectric material and the inorganic substrate.

Preferably, the release layer is of a composition having a solubility or an etching profile different from the dielectric material and/or substrate so as to facilitate separation of the sensor component from the substrate. In one aspect, the release layer is a photosensitive material that changes its solubility upon exposure to actinic radiation. Thus, for example, the release layer may be initially insoluble in aqueous media or aqueous base (cast from an organic solvent), but upon exposure to actinic radiation, the release layer becomes readily soluble in aqueous media/base. After depositing the release layer cast with an organic solvent, the layer is flood exposed to render the release layer insoluble in organic solvent and soluble in aqueous media. By using dielectric materials that are insoluble in aqueous media provides for dissolution of the release layer and separation of dielectric layer of the fabricated sensor component from the substrate. Examples of materials suitable as release layers would include, for example, positive novalak/diazonaphthaquinone resists and/or chemically amplified photoresists (partially blocked vinylphenol chemically amplified resists, polybutene 1-sulfone and the like) generally know in the MEMs/IC manufacture art.

In another aspect, an inorganic thin-film may be used as the release layer. For example, a thin film of silicon oxide or silica glass may be used as the release layer for an inorganic substrate (e.g., silicon wafer). In this aspect, the fabricated sensor component may be released by HF (hydrofluoric acid) wet etching. Since HF will attack exposed metal electrodes and pads, a photoresist protection layer may be used to protect the sensor surface during HF wet etching. The thin-film inorganic release layer may of a thickness of about 10 nm to about 500 nm. Other thickness may be used. The film may be deposited by sputtering, for example.

In another aspect, a metal sacrificial layer may be used to release the electrochemical sensor component from a substrate. For example, titanium or chrome (100-500 nm) may be deposited by sputtering or evaporative techniques on a substrate such as silicon wafer. Then, a thin layer of aluminum (300-1000 nm) may be deposited on the Ti or Cr layer. After partial or complete fabrication of polymer sensor the aluminum layer may be etched away to release the sensors from substrate. The thin aluminum layer may be etched chemically or electrochemically. For example, the substrate may be electrochemically etched by immersion in a strong electrolyte solution, such as 1-2 M potassium chloride or sodium chloride at room temperature. The anodic metal dissolution is carried out by applying an anodic DC voltage of 0.5-1.0 V on the aluminum layer vs. a larger Pt or carbon counter electrode. After aluminum is dissolved, more stable and inert chrome or titanium layer remains on the substrate, thus releasing the polymer sensors. The metal release layer may of a thickness of about 10 nm to about 500 nm. Other thickness may be used. The film may be deposited by sputtering, for example.

In another aspect, the release layer is a pressure sensitive adhesive (PSA) or the like, disposed between the first flexible dielectric layer and the substrate such that the sensors may be mechanically removed from the substrate. Preferably, the pressure sensitive adhesive is disposed essentially completely between the first flexible dielectric layer and the substrate. In The PSA may be deposited by casting, dipping, or spin coating, for example.

The fabrication of the analyte sensor comprises depositing dielectric material on conductive material formed on the substrate and defining perimeters therein to isolate continuously connected electrodes, traces and contacts. For example, the dielectric material may be patterned to provide for subsequent formation of one or more isolated, continuously connected electrodes, traces and contact pads. Additional dielectric layers are used for defining openings over at least one of the electrodes and contact pads. Patterning of the dielectric material may be performed using known photoresist/mask techniques. For example, a polyimide or polyepoxide photoresist material may be used as the dielectric. In one aspect, the dielectric material comprises multiple polymeric layers of suitable material characteristics and properties. Thus, the fabrication process may comprise deposition of a first polymer layer formed of a suitable dielectric material such as polyimide, parylene, polydimethylsiloxane, or polyepoxide, at a thicknesses suitable for electrical isolation of the sensor components and/or for providing sufficient flexibility and durability during fabrication and intended use. The dielectric polymer layers may be deposited at thicknesses of about 15 μm, 10 μn, 5 um, 1 um or less. Other thicknesses of dielectric polymer layer may be used. The dielectric polymer layer may be deposited using known methods such as spin coating, casting and the like. Preferably, the dielectric polymer is photosensitive such that it may be imaged using photolithographic techniques. Thus, in one aspect, one or more of the dielectric polymer layers are photosensitive (positive or negative photoresists). For example, a photosensitive polyimide or photosensitive polyepoxide may be used and the perimeters formed therein using photolithographic methods and etching/developing, or alternatively, by laser ablation. Processes of forming the perimeters in the dielectric may include image reversal using a positive photoresist.

Thus, in one embodiment, a fabrication process comprises coating a first flexible dielectric layer on a semiconductor substrate having disposed thereon a release layer as described above. A conductive material is then deposited over the first flexible dielectric polymer layer (optionally over a previously applied adhesion layer). A photosensitive mask layer with suitable etching properties is then deposited over the conductive material and patterned to define the perimeters of the individual electrodes, traces and contact pads. Etching of the photosensitive mask layer and conductive material provides a plurality of isolated continuously connected electrodes, traces and contact pads. Alternatively, the conductive layer may be laser ablated to define the features. A second flexible dielectric is applied to the surface of the conductive material (optionally over an adhesive layer). Photolithography or laser ablation may be used to create the openings over the electrodes and to expose the contact pads. An analyte sensing membrane may be deposited into one or more openings over the electrodes to provide a plurality of electrochemical sensor components on the substrate. The dielectric layers, electrodes and the defined openings forming the electrochemical sensor components may be lifted off the substrate for deposition of an analyte sensing membrane and/or coupling with a flex circuit or medical device. The individual sensors may be separated from each other using laser cutting or dicing methods, for example.

The flexibility of the fabricated sensor component can be controlled by the thickness of the first flexible dielectric polymer layer. The flexibility may be adjusted for a particular application, such as, for example, for introduction into a catheter, for, example, to accommodate tortuous path introduction into a subject.

In another embodiment, a fabrication process comprises coating a first flexible dielectric polymer layer on a semiconductor substrate having deposited thereon a release layer. A photosensitive mask layer is then coated over the first dielectric polymer layer. The mask layer may be lithographically patterned to provide one or more isolated openings and/or trenches for receiving conductive material. For example, a positive or negative photoresist material may be used and exposed/developed to provide one or more openings and/or trenches in the mask layer. A conductive material is then deposited over the mask layer (optionally over a previously applied adhesion layer) and into the openings/trenches defining the plurality of individual continuously connected electrodes, traces and contact pads. Removal of any excess conductive material on the surface of the mask may be accomplished by etching or chemical polishing techniques. The mask layer is then removed by solvent or etching to provide isolated features defining the electrodes traces and contact pads. Then a second, preferably, photosensitive dielectric layer is applied over the isolated conductive material and openings are defined therein over one or more of the electrodes/contact pads using photolithographic methods or laser ablation. An analyte sensing membrane may be deposited into one or more openings over the electrodes and/or draping or encapsulating the membrane to provide a plurality of electrochemical sensors on the substrate. The dielectric layers and the defined openings forming the electrochemical sensors may be lifted off the substrate. The individual sensors may be separated from each other using laser cutting or dicing methods, for example.

In yet another embodiment, a fabrication process comprises depositing a first flexible dielectric material directly on a semiconductor substrate and then coating the dielectric with a conductive material (optionally over a previously applied adhesion layer) followed by coating with a photosensitive mask layer. Photolithography or laser ablation may be used to create the perimeters of the continuously connected conductive electrode, contact pads and traces in the photosensitive mask layer as described above. The plurality of individual electrodes, traces, and contact pads are then formed by developing and/or etching of the mask and excess conductive material. A second flexible dielectric layer is then applied and openings are formed over one or more of the isolated continuously connected electrodes and contact pads using photolithographic methods or laser ablation. In this aspect, the fabricated sensor has a set rigidity based on the thickness of the semiconductor substrate. The rigidity may be adjusted for a particular application, such as by etching or polishing the semiconductor substrate until a desired thickness is obtained. Alternatively, the fabrication process may comprise coating a first flexible dielectric material on the substrate and a second photosensitive dielectric material on the first flexible dielectric material (optionally over a previously applied adhesion layer). The second polymer layer may be patterned to provide one or more isolated openings, trenches and/or vias for receiving the conductive material, as described above.

The openings, trenches and/or vias of the sensor may be fabricated with an aspect ratio (height to width) of between about 1:100 to about 100:1. Preferably, the aspect ratio is between 1:10 and 10:1 and more preferably, the aspect ratio is between 1:5 and 5:1. In one aspect, the aspect ratio is high (e.g., 2:1 or greater) such that the analyte sensing membrane is contained or otherwise positioned within the opening and includes being flush with the surface of the dielectric material defining the opening. In other aspects, the aspect ratio is low (e.g., 1:2 or greater) such that the analyte sensing membrane drapes over the opening and includes filling the opening with the analyte sensing membrane.

Other MEMs/IC fabrication techniques may be used to provide a semiconductor substrate having a dielectric material insulating traces connecting electrodes and contact pads and for defining openings over one or more of the electrodes to receive a sensing membrane and for defining openings over one or more of the contact pads for electrical connection therewith.

Fabrication of the electrodes, traces and contact pads may comprise successive deposition of thin films of material, including, for example, releasing and/or adhesion layers, dielectric material, conductive material, and photosensitive material. Deposition of the release layer and dielectric material may be by casting or spin coating. Deposition of the adhesion layer and conductive material onto the substrate or dielectric material is accomplished by convention methods (e.g., chemical vapor deposition, epitaxy, electrodeposition, or thermal oxidation) or by physical reaction-based approaches (evaporation, sputtering, casting, e-beam, electroless plating, or electroplating). Electrode, trace, and contact pad conductive material is formed over the first polymer layer and optional metal adhesion layer by sputtering, chemical vapor deposition (CVD), or electro- or electroless-plating methods. The electrode, trace, and contact pad conductive material may be deposited with a thickness of about 500 nm or more. The electrode, trace, and contact pad conductive material may be patterned using known techniques to provide the desired sensor architecture.

The electrodes, traces, and contact pads may be made of different conductive materials. Electrode, trace, and contact pad conductive material may be deposited by sputtering, chemical vapor deposition (CVD), or electro- or electroless-plating methods. The conductive material may be deposited with a thickness of about 500 nm or more. The conductive material may be patterned using known techniques to provide the desired sensor architecture, including, for example, electrodes, traces, and contact pads. In one aspect, the working electrode may be a platinum based enzyme electrode, i.e. an electrode having disposed thereon an analyte sensing membrane. The same or different conductive materials may be used for any of the electrode, trace, and contact pad structures. For example, the contact pads may be formed of a material such as gold (Au) platinum (Pt), palladium (Pd), ruthenium (Ru), rhodium (Rh), iridium (Ir), carbon (C), or other material that resists oxidation. The traces may be formed of any suitable conductive material, such as gold (Au) platinum (Pt) or copper (Cu). The electrode material may of any suitable material, and for example, may be formed of platinum (Pt), gold (Au), palladium (Pd), ruthenium (Ru), rhodium (Rh), iridium (Ir), silver (Ag), carbon (C) and their alloys or oxides. Conducting polymers, such as polypyrrole (PPy), polyaniline (PANi), polythiophene, poly(3,4-ethylenedioxythiophene) (PEDOT) or their derivatives can also be used to form the electrodes, traces, or contact pads.

A reference electrode may be used to input a bias signal into the amperometric sensor. In some embodiments, the reference electrode is formed by depositing silver (Ag) in one of the fabricated openings and then converting the silver to silver chloride (Ag/AgCl), either chemically or electrochemically. Masking techniques generally known in IC manufacturing may be used to selectively deposit different metals/materials to form the various electrodes (e.g., working, counter and reference electrodes).

Optionally, an adhesion layer may be provided over the dielectric material and/or conductive material to facilitate the bonding and/or improve adhesion to an adjacent layer. Typically, adhesion layers are used to improve adhesion between metals and polymers. Adhesion layers may be formed by sputtering or plating methods, for example. For metal/polymer interfaces, the adhesion layer is preferably metallic. The metallic adhesion layers can be of any suitable material, such as titanium (Ti), nickel (Ni), tungsten (W), chromium (Cr), or combination of these metals or alloys for example, and may be deposited by sputtering, chemical vapor deposition (CVD), or electro- or electroless-plating methods. In one aspect, the metallic adhesion layer may be of titanium (Ti) with thickness in the area of 10-100 nm, however, other thicknesses may be used. The adhesion layer may be patterned to provide for selective deposition of the conductive material.

Fabrication of the various components of the sensor, such as the arrangement of the electrodes, traces and contact pads, as well as the deposition of the conductive material are advantageously carried out using MEMs/IC processes. Various shaped sensors with various dimensions ranging from micrometers to millimeters can be batch manufactured. Sensor electrodes made of a pure metal such as platinum (Pt) may have higher sensitivity than alloys and/or conductive inks, thereby providing for higher signal to noise ratios. One advantage of IC/MEMs fabrication technology as opposed to conventional silk screening or other electrode deposition methods of fabricating sensors may be greater reproducibility from electrode to electrode and panel of sensors to panel of sensors. Reproducibility of electrodes is important at least in terms of manufacture of working and blank electrodes, as accurate structural matching of these two electrodes in a sensor reduces electrical output offset between the electrodes.

Various shaped sensors with various dimensions ranging from micrometers to millimeters can be batch manufactured. Sensor electrodes made of a pure metal such as platinum (Pt) may have higher sensitivity than alloys and/or conductive inks, thereby providing for higher signal to noise ratios, and therefore may be preferred. One advantage of IC/MEMs fabrication technology as opposed to conventional silk screening or other electrode deposition methods of fabricating sensors may be greater reproducibility from electrode to electrode and panel of sensors to panel of sensors. Reproducibility of electrodes is important at least in terms of manufacture of working and blank electrodes, as accurate structural matching of these two electrodes in a sensor reduces electrical output offset between the electrodes.

Different structural embodiments of the sensor structure and spatial arrangement of electrode, trace and contact pad may be used. For example, electrodes of different shapes and different dimensions may be employed. Two smaller counter electrodes may be used, as opposed to a larger single counter electrode, while maintaining a larger surface area ratio between the counter electrode and working electrode. The working electrode(s) may be positioned between a counter electrode and a reference electrode.

It is understood that the basic layout of the sensor elements (electrodes, traces, contacts) may be constructed in a number of ways, each of which results in at least one isolated electrode connected to at least one contact pad by one or more traces. Provided hereinafter are exemplary processes that result in an arrangement of sensor components resulting in the aforementioned architecture. These exemplary processes are provided as such, and are not intended to limit the embodiments disclosed herein.

Additional electrode and or traces and contact pads may be employed, for example, to provide a temperature sensor. Multiple analyte detecting "openings" may also be prepared on a single sensor. After formation of the openings over the electrodes, the electrochemical sensor component would be ready for receiving the analyte sensing membrane as discussed below.

Electrode and Dielectric Surface Pretreatment

In one aspect, the fabrication process comprises treating the electroactive surface of the conductive material prior to application of the subsequent analyte sensing membrane. Surface treatments may include for example, chemical, gas plasma or laser treatment of at least a portion of the electroactive surface. By way of example, the electrodes may be chemically or covalently contacted with one or more adhesion promoting agents. Adhesion promoting agents may include for example, aminoalkylalkoxylsilanes, epoxyalkylalkoxylsilanes, and the like. For examples, one or more of the electrodes may be chemically or covalently contacted with a solution containing 3-glycidoxypropyltrimethoxysilane. Alternatively, the electrode surface may be contacted with a gas plasma, for example, an oxygen plasma for a time, concentration and at a power sufficient to improve the electrical response of the sensor. Other plasma gases may be used such as air, nitrogen, ammonia, carbon dioxide, water and combinations thereof.

In another aspect, the fabrication process comprises treating the surface of the dielectric material prior to application of the subsequent analyte sensing membrane. Surface treatments may include for example, physical, chemical or combinations of physical and/or covalent/non-covalent, and/or ionic bonding treatments. By way of example, physical treatments may be sanding, grinding, etching or other surface roughening methods to increase the surface area of at least a portion of the dielectric surface. By way of example, chemical treatments may include chemical, gas plasma, or laser exposure of at least a portion of the dielectric surface. Thus, the surface of the dielectric material may be chemically or covalently contacted with one or more adhesion promoting agents. Adhesion promoting agents may include for example, aminoalkylalkoxylsilanes, epoxyalkylalkoxylsilanes and the like. For examples, one or more of the electrodes may be chemically or covalently contacted with a solution containing 3-glycidoxypropyltrimethoxysilane. Alternatively, the surface of the dielectric material may be contacted with a gas plasma, for example, an oxygen plasma for a time, concentration and at a power sufficient to improve the adhesion of the analyte sensing membrane. Other plasma gases may be used such as air, nitrogen, ammonia, carbon dioxide, water and combinations thereof. Covalent coupling of the analyte sensing membrane to the plasma treated surface of the dielectric material may be performed using known coupling methods, for example, 1-ethyl-3(3-dimethyl aminopropyl)carbodiimide hydrochloride (EDC) or N-hydroxysuccinimide or other water-soluble carbodiimides, and may be employed with enhancers such as N-hydroxysulfosuccinimide (sulfo-NHS), although other suitable enhancers, such as N-hydroxysuccinimide (NHS), can alternatively be used. Thus, in one aspect, the surface of one dielectric material may be different from the surface of another dielectric material used for fabricating the sensor.

Interference Layer

In one aspect, the fabrication process comprises the deposition of an interference layer to prevent or reduce migration of chemical species through the analyte sensing membrane. Interferents may be molecules or other species that may be reduced or oxidized at the electrochemically reactive surfaces of the sensor, either directly or via an electron transfer agent, to produce a false positive analyte signal (e.g., a non-analyte-related signal). This false positive signal generally causes the subject's analyte concentration to appear higher than the true analyte concentration. For example, in a hypoglycemic situation, where the subject has ingested an interferent (e.g., acetaminophen), the artificially high glucose signal may lead the subject or health care provider to believe that they are euglycemic or, in some cases, hyperglycemic. As a result, the subject or health care provider may make inappropriate or incorrect treatment decisions.

In one aspect, the fabrication process comprises includes depositing an interference layer that substantially restricts or eliminates the passage there through of one or more interfering species. Interfering species for a glucose sensor include, for example, acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, urea and uric acid. The interference layer may be less permeable to one or more of the interfering species than to a target analyte species.

In one aspect, the interference layer is formed from one or more cellulosic derivatives. In one aspect, mixed ester cellulosic derivatives may be used, for example, cellulose acetate butyrate, cellulose acetate phthalate, cellulose acetate propionate, cellulose acetate trimellitate, as well as their copolymers and terpolymers, with other cellulosic or non-cellulosic monomers, including cross-linked variations of the above. Other polymers, such as polymeric polysaccharides having similar properties to cellulosic derivatives, may be used as an interference material or in combination with the above cellulosic derivatives. Other esters of cellulose may be blended with the mixed ester cellulosic derivatives.

In one aspect, the interference layer is formed from cellulose acetate butyrate. Cellulose acetate butyrate is a cellulosic polymer having both acetyl and butyl groups, and hydroxyl groups. A cellulose acetate butyrate having about 35% or less acetyl groups, about 10% to about 25% butyryl groups, and hydroxyl groups making up the remainder may be used. A cellulose acetate butyrate having from about 25% to about 34% acetyl groups and from about 15 to about 20% butyryl groups may also be used, however, other amounts of acetyl and butyryl groups may be used. A preferred cellulose acetate butyrate contains from about 28% to about 30% acetyl groups and from about 16 to about 18% butyryl groups.

Cellulose acetate butyrate with a molecular weight of about 10,000 Daltons to about 75,000 Daltons is preferred, preferably from about 15,000, 20,000, or 25,000 Daltons to about 50,000, 55,000, 60,000, 65,000, or 70,000 Daltons, and more preferably about 65,000 Daltons is employed. In certain embodiments, however, higher or lower molecular weights may be used or a blend of two or more cellulose acetate butyrates having different molecular weights may be used.

A plurality of layers of cellulose acetate butyrate may be combined to form the interference layer in some embodiments, for example, two or more layers may be employed. It may be desirable to employ a mixture of cellulose acetate butyrates with different molecular weights in a single solution, or to deposit multiple layers of cellulose acetate butyrate from different solutions comprising cellulose acetate butyrate of different molecular weights, different concentrations, and/or different chemistries (e.g., wt % functional groups). Additional substances in the dispensing solutions or dispersions may be used, e.g., dispensing aids, defoamers, surface tension modifiers, functionalizing agents, crosslinking agents, other polymeric substances, substances capable of modifying the hydrophilicity/hydrophobicity of the resulting layer, and the like.

The dispensing of the interference material may be performed using any known thin film technique. For example, the interference material may be dispensed into the well of the electrochemical sensor component by micro-pipetting, spraying, casting, coating, or dipping directly to the electroactive surface(s). Two, three or more layers of interference material may be formed by the sequential application and curing and/or drying of the casting solution.

The concentration of solids in the casting solution may be adjusted to deposit a sufficient amount of solids or film on the electrode in one layer (e.g., in one dip or spray) to form a layer sufficient to block an interferant with an oxidation or reduction potential otherwise overlapping that of a measured species (e.g., $H_2O_2$), measured by the sensor. For example, the casting solution's percentage of solids may be adjusted such that only a single layer is required to deposit a sufficient amount to form a functional interference layer that substantially prevents or reduces the equivalent glucose signal of the interferant measured by the sensor. A sufficient amount of interference material would be an amount that substantially prevents or reduces the equivalent glucose signal of the interferant of less than about 30, 20 or 10 mg/dl. By way of example, the interference layer is preferably configured to substantially block about 30 mg/dl of an equivalent glucose signal response that otherwise would be produced by acetaminophen by a sensor without an interference layer. Such equivalent glucose signal response produced by acetaminophen would include a therapeutic dose of acetaminophen. Any number of coatings or layers formed in any order may be suitable for forming the interference layer of the sensor disclosed herein.

In one aspect, the fabrication process comprises depositing the interference layer either directly onto the electroactive surfaces of the sensor or onto a material or layer in direct contact with the surface of the electrode, for example, a hydrophilic polymer layer.

The interference layer may be applied to provide a thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 1, 1.5 or 2 microns to about 2.5 or 3 microns. Thicker membranes may also be desirable in certain embodiments, but thinner membranes may be generally preferred because they generally have a lower affect on the rate of diffusion of hydrogen peroxide from the enzyme membrane to the electrodes.

Enzyme Layer

In one aspect, the fabrication process comprises depositing an analyte sensing membrane comprising an enzyme layer. The enzyme layer may comprise a hydrophilic polymer. It has been surprisingly found that the configuration where the enzyme layer is deposited directly onto at least a portion of the interference layer may substantially eliminate the need for an intervening layer between the interference layer and the enzyme layer while still providing a rapid and accurate signal representative of the analyte. In one aspect, the enzyme layer comprises an enzyme deposited directly onto at least a portion of the interference layer.

In one aspect, the enzyme layer comprises a enzyme and a hydrophilic polymer selected from poly-N-vinylpyrrolidone (PVP), poly-N-vinyl-3-ethyl-2-pyrrolidone, poly-N-vinyl-4,5-dimethyl-2-pyrrolidone, polyacrylamide, poly-N,N-dimethylacrylamide, polyvinyl alcohol, polymers with pendent ionizable groups (polyelectrolytes) and copolymers thereof. Preferably, the enzyme layer comprises poly-N-vinylpyrrolidone. Most preferably, the enzyme layer comprises glucose oxidase, poly-N-vinylpyrrolidone and optionally an amount of crosslinking agent sufficient to immobilize the enzyme.

The molecular weight of the hydrophilic polymer of the enzyme layer is preferably such that fugitive species are prevented or substantially inhibited from leaving the sensor environment and more particularly, fugitive species are prevented or substantially inhibited from leaving the enzyme's environment when the sensor is initially deployed.

The hydrophilic polymer of the enzyme layer may further include at least one protein and/or natural or synthetic material. For example, the enzyme layer may further include, for example, serum albumins, polyallylamines, polyamines and the like, as well as combination thereof.

The enzyme of the enzyme layer is preferably immobilized in the sensor. The enzyme may be encapsulated within the hydrophilic polymer and may be cross-linked or otherwise immobilized therein. The enzyme may be cross-linked or otherwise immobilized optionally together with at least one protein and/or natural or synthetic material. In one aspect, the hydrophilic polymer-enzyme composition comprises glucose oxidase, bovine serum albumin, and poly-N-vinylpyrrolidone. The composition may further include a cross-linking agent, for example, a dialdehyde such as glutaraldehdye, to cross-link or otherwise immobilize the components of the composition.

In one aspect, other proteins or natural or synthetic materials may be substantially excluded from the hydrophilic polymer-enzyme composition of the enzyme layer. For example, the hydrophilic polymer-enzyme composition may be substantially free of bovine serum albumin. Bovine albumin-free compositions may be desirable for meeting various governmental regulatory requirements. Thus, in one aspect, the enzyme layer comprises glucose oxidase and a sufficient amount of cross-linking agent, for example, a dialdehyde such as glutaraldehdye, to cross-link or otherwise immobilize the enzyme. In other aspect, the enzyme layer comprises glucose oxidase, poly-N-vinylpyrrolidone and a sufficient amount of cross-linking agent to cross-link or otherwise immobilize the enzyme.

The enzyme layer thickness may be from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns. Preferably, the enzyme layer is deposited by spray or dip coating, however, other methods of forming the enzyme layer may be used. The enzyme layer may be formed by micro-pipetting, dip coating and/or spray coating one or more layers at a predetermined concentration of the coating solution, insertion rate, dwell time, withdrawal rate, and/or desired thickness.

Flux Limiting Layer

In one aspect, the fabrication process comprises disposing a flux limiting layer over the subsequent layers described above, where the flux limiting layer alters or changes the rate of flux of one or more of the analytes of interest. Although the following description is directed to a flux limiting layer for an electrochemical glucose sensor, the flux limiting layer may be modified for other analytes and co-reactants as well.

In one aspect, the flux limiting layer comprises a semi-permeable material that controls the flux of oxygen and glucose to the underlying enzyme layer, preferably providing oxygen in a non-rate-limiting excess. As a result, the upper limit of linearity of glucose measurement is extended to a much higher value than that which is achieved without the flux limiting layer. In one embodiment, the flux limiting layer exhibits an oxygen to glucose permeability ratio of from about 50:1 or less to about 400:1 or more, preferably about 200:1. Other flux limiting layers may be used or combined, such as a membrane with both hydrophilic and hydrophobic polymeric regions, to control the diffusion of analyte and optionally co-analyte to an analyte sensor. For example, a suitable membrane may include a hydrophobic polymer matrix component such as a polyurethane, or polyetherurethaneurea. In one aspect, the material that forms the basis of the hydrophobic matrix of the layer can be any of those known in the art as appropriate for use as membranes in sensor devices and as having sufficient permeability to allow relevant compounds to pass through it, for example, to allow an oxygen molecule to pass through the layer from the sample under examination in order to reach the active enzyme or electrochemical electrodes. For example, non-polyurethane type layers such as vinyl polymers, polyethers, polyesters, polyamides, inorganic polymers such as polysiloxanes and polycarbosiloxanes, natural polymers such as cellulosic and protein based materials, and mixtures or combinations thereof may be used.

In one aspect, the flux limiting layer comprises a polyethylene oxide component. For example, a hydrophobic-hydrophilic copolymer comprising polyethylene oxide is a polyurethane polymer that includes about 20% hydrophilic polyethylene oxide. The polyethylene oxide portions of the copolymer are thermodynamically driven to separate from the hydrophobic portions (e.g., the urethane portions) of the copolymer and the hydrophobic polymer component. The 20% polyethylene oxide-based soft segment portion of the copolymer used to form the final blend affects the water pick-up and subsequent glucose permeability of the membrane.

In one aspect, the flux limiting layer substantially excludes condensation polymers such as silicone and urethane polymers and/or copolymers or blends thereof. Such excluded condensation polymers typically contain residual heavy metal catalytic material that may otherwise be toxic if leached and/or difficult to completely remove, thus rendering their use in such sensors undesirable for safety and/or cost.

In another aspect, the material that comprises the flux limiting layer may be a vinyl polymer appropriate for use in sensor devices having sufficient permeability to allow relevant compounds to pass through it, for example, to allow an oxygen molecule to pass through in order to reach the active enzyme or electrochemical electrodes. Examples of materials which may be used to make the flux limiting layer include vinyl polymers having vinyl ester monomeric units. In a preferred embodiment, a flux limiting layer comprises poly ethylene vinyl acetate (EVA polymer). In other aspects, the flux limiting layer comprises poly(methylmethacrylate-co-butyl methacrylate) blended with the EVA polymer. The EVA polymer or its blends may be cross-linked, for example, with diglycidyl ether. Films of EVA are very elastomeric, which may provide resiliency to the sensor for navigating a tortuous path, for example, into venous anatomy.

The EVA polymer may be provided from a source having a composition anywhere from about 9 wt % vinyl acetate (EVA-9) to about 40 wt % vinyl acetate (EVA-40). The EVA polymer is preferably dissolved in a solvent for dispensing into the well formed in the sensor or sensor assembly. The solvent should be chosen for its ability to dissolve EVA polymer, to promote adhesion to the sensor substrate and enzyme electrode, and to form a solution that may be effectively dispensed (e.g. micro-pipette, spray, dip coating, spin coating). Solvents such as cyclohexanone, paraxylene, and tetrahydrofuran may be suitable for this purpose. The solution may include about 0.5 wt % to about 6.0 wt % of the EVA polymer. In addition, the solvent should be sufficiently volatile to evaporate without undue agitation to prevent issues with the underlying enzyme, but not so volatile as to create problems with the dispensing process. In a preferred embodiment, the vinyl acetate component of the flux limiting layer includes about 20% vinyl acetate. In preferred embodiments, the flux limiting layer is deposited onto the enzyme layer to yield a layer thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 5, 5.5 or 6 microns to about 6.5, 7, 7.5 or 8 microns. The flux limiting layer may be deposited onto the enzyme layer, for example, by spray coating or dip coating. In one aspect, the flux limiting layer is deposited on the enzyme layer by coating a solution of from about 1 wt. % to about 5 wt. % EVA polymer and from about 95 wt. % to about 99 wt. % solvent.

In one aspect, an electrochemical analyte sensor fabricated as described above is provided comprising an isolated electrode formed on an inorganic substrate, the electrode isolated between first and second polymer layers arranged on the inorganic substrate, the sensor being encapsulated in a flux limiting layer covering the analyte sensing membrane layers and the underlying isolated electrode. Thus, the flux limiting layer formed from an EVA polymer may serve as a flux limiter at the top of the electrode, but also serve as a sealant or encapsulant at the enzyme/electrode boundary and at the electrode/dielectric boundary.

Additional Layers

The fabrication process of the electrochemical sensor described herein may further comprise depositing additional layers that provide specific functions for improving the performance of the sensor. For example, additional layers may provide for manipulation of various biological processes when used in vivo in a subject. The additional layer may provide shielding of external electrical or magnetic fields (EMF or RF). The additional layers may be adjacent to or cover at least a part of the flux limiting layer. The additional layers may include hydrophilic polymer membranes, polymers with pendent ionizable groups (polyelectrolytes) and copolymers thereof.

In one aspect, the additional layer is a hydrophilic polymer membrane that is essentially water-insoluble. As used herein, the phase "water-insoluble" refers to a hydrophilic polymer membrane that, when exposed to an excess of water, may swell or otherwise absorb water to an equilibrium volume, but does not dissolve into the aqueous solution. As such, a water-insoluble material generally maintains its original physical structure during the absorption of the water and, thus, must have sufficient physical integrity to resist flow and diffusion away or with its environment. As used herein, a material will be considered to be water insoluble when it substantially resists dissolution in excess water to form a solution, and/or losing its initial, film form and resists becoming essentially molecularly dispersed throughout the water solution. In one aspect, the hydrophilic polymer membrane is coated over the flux limiting layer and will not degrade or diffuse away from the flux limiting layer during use, for example, during in vivo use.

Bioactive Agent Layer and Active Agents

In some alternative embodiments, a bioactive agent layer may be used. The bioactive agent layer may be optionally incorporated into any of the above described layers, such that the bioactive diffuses out into the biological environment adjacent to the sensor. Additionally or alternately, a bioactive agent may be administered locally at the exit-site or implantation-site. Suitable bioactive agents include active agents that modify the subject's tissue response to any of the sensor or components thereof. For example, bioactive agents may be selected from anti-inflammatory agents, anti-infective agents, anesthetics, inflammatory agents, growth factors, immunosuppressive agents, antiplatelet agents, anti-coagulants, anti-proliferates, ACE inhibitors, cytotoxic agents, anti-barrier cell compounds, anti-vascularization-inducing compounds, anti-sense molecules, or mixtures thereof. The bioactive agent layer may be employed in the analyte sensor to prevent coagulation within or on the sensor (e.g., within or on the catheter or within or on the sensor). Suitable bioactive agents that function as anticoagulants for incorporation into or on the sensor include, but are not limited to, vitamin K antagonists (e.g., Acenocoumarol, Clorindione, Dicumarol (Dicoumarol), Diphenadione, Ethyl biscoumacetate, Phenprocoumon, Phenindione, Tioclomarol, or Warfarin), heparin group anticoagulants (e.g., Platelet aggregation inhibitors: Antithrombin III, Bemiparin, Dalteparin, Danaparoid, Enoxaparin, Heparin, Nadroparin, Parnaparin, Reviparin, Sulodexide, Tinzaparin), other platelet aggregation inhibitors (e.g., Abciximab, Acetylsalicylic acid (Aspirin), Aloxiprin, Beraprost, Ditazole, Carbasalate calcium, Cloricromen, Clopidogrel, Dipyridamole, Epoprostenol, Eptifibatide, Indobufen, Iloprost, Picotamide, Ticlopidine, Tirofiban, Treprostinil, Triflusal), enzymes (e.g., Alteplase, Ancrod, Anistreplase, Brinase, Drotrecogin alfa, Fibrinolysin, Protein C, Reteplase, Saruplase, Streptokinase, Tenecteplase, Urokinase), direct thrombin inhibitors (e.g., Argatroban, Bivalirudin, Desirudin, Lepirudin, Melagatran, Ximelagatran, other antithrombotics (e.g., Dabigatran, Defibrotide, Dermatan sulfate, Fondaparinux, Rivaroxaban) and the like. In one aspect, the bioactive agent layer comprises at least one active agent selected from the group consisting of vitamin K antagonists, heparin group anticoagulants, platelet aggregation inhibitors, enzymes, direct thrombin inhibitors, Dabigatran, Defibrotide, Dermatan sulfate, Fondaparinux, and Rivaroxaban.

The bioactive agent may be incorporated into the membrane of the preferred embodiments described above. In some embodiments, the bioactive agent is incorporated at the time of manufacture of the analyte sensing membrane. For example, the bioactive agent can be blended prior to or subsequent to analyte sensing membrane manufacture, for example, by coating, imbibing, solvent-casting, or sorption of the bioactive agent into the analyte sensing membrane. Although the bioactive agent is preferably incorporated into the analyte sensing membrane, in some embodiments the bioactive agent can be administered concurrently with, prior to, or after insertion of the device comprising the sensor (e.g., intravascularly), for example, by oral administration, or locally, for example, by subcutaneous injection near the implantation site. A combination of the bioactive agent in the analyte sensing membrane and the bioactive agent administration locally and/or systemically may be preferred in certain aspects.

The bioactive agent may be incorporated or disposed only into or onto a portion of the analyte sensing membrane adjacent to the sensing region of the device, over the entire surface of the device except over the sensing region, or any combination thereof. Such arrangement of bioactive agent may be helpful in controlling different mechanisms and/or stages of thrombus formation. However, the bioactive agent may be incorporated into the analyte sensing membrane, so that the bioactive agent can diffuse through the analyte sensing membrane and into the host circulatory system. The bioactive agent can be deposited in or on the analyte sensing membrane, for example, by coating, filling, or solvent casting. The bioactive agent can be incorporated into a polymer using techniques such as described above, and the polymer can be used to form one of the layers of the analyte sensing membrane, coatings on the analyte sensing membrane, portions of the analyte sensing membrane, and/or any portion of the sensor.

A carrier may be used for the bioactive agent. The carrier may include one or more of collagen, a particulate matrix, a resorbable or non-resorbable matrix, a controlled-release matrix, and/or a gel. The carrier may include a reservoir encapsulating a microcapsule comprising a bioactive agent. The bioactive agent may be cross-linked with the analyte sensing membrane or sorbed into the analyte sensing membrane, for example, by adsorption, absorption, or imbibing.

The bioactive agents can be chosen for short-term release to aid or overcome factors associated with short-term effects (e.g., acute inflammation and/or thrombosis) of sensor insertion, for example. The bioactive agents may be chosen for long-term release to aid or overcome factors associated with long-term effects, for example, chronic inflammation or build-up of fibrotic tissue and/or plaque material. The bioactive agents may combine short- and long-term release to provide the benefits of both. Thus, the bioactive agents may be provided in a controlled, sustained or extended release form, wherein "controlled," "sustained," or "extended" release is inclusive of continuous or discontinuous, linear or non-linear release profiles. This can be accomplished using one or more types of polymer compositions, drug loadings, selections of excipients or degradation enhancers, or other modifications, administered alone, in combination or sequentially to produce the desired effect.

The bioactive agent can be incorporated into a hydrogel and coated or otherwise deposited in or on the analyte sensing membrane. Some hydrogels suitable for use include cross-linked, hydrophilic, three-dimensional polymer networks that are permeable to the bioactive agent and/or release the bioactive agent based on an external stimulus.

The amount of bioactive agent into the analyte sensing membrane can depend upon several external variables. For example, the bioactive agent dosage and duration can vary with the intended use of the analyte sensing membrane, for example, the intended length of use of the device; differences in effective dose of bioactive agent among patients in the; location and administration of the bioactive agent; and release rates associated with bioactive agents. One skilled in the art will appreciate the variability in loading levels of the bioactive agent for at least the reasons described above.

When the bioactive agent is incorporated into the analyte sensing membrane without a carrier, the level of loading of the bioactive agent into the analyte sensing membrane can vary depending upon the chemical and/or physical nature of the bioactive agent. The level of loading of the bioactive agent is preferably sufficiently high such that a biological effect (e.g., thrombosis prevention) is obtained. The level of loading (based on the weight of bioactive agent(s), analyte sensing membrane, and other substances present) is from about 1 ppm or less to about 1000 ppm or more, preferably from about 2, 3, 4, or 5 ppm up to about 10, 25, 50, 75, 100, 200, 300, 400, 500, 600, 700, 800, or 900 ppm. In certain embodiments, the level of loading can be 1 wt. % or less up to about 50 wt. % or more, preferably from about 2, 3, 4, 5, 6, 7, 8, 9, 10, 15, or 20 wt. % up to about 25, 30, 35, 40, or 45 wt. %.

When the bioactive agent is incorporated into the analyte sensing membrane with a carrier, the carrier concentration can be optimized by loading with one or more test loadings of the bioactive agent. The carrier may contain from about 0.1 or less to about 50 wt. % or more of the bioactive agent(s), preferably from about 0.2, 0.3, 0.4, 0.5, 0.6, 0.7, 0.8, or 0.9 wt. % to about 6, 7, 8, 9, 10, 15, 20, 25, 30, 35, 40, or 45 wt. % or more bioactive agent(s), more preferably from about 1, 2, or 3 wt. % to about 4 or 5 wt. % of the bioactive agent(s). Substances that are not bioactive and/or act synergistically with the bioactive agent can also be used.

Flexible Substrate Sensor Assembly

In one aspect, the method disclosed herein includes the step of coupling the contacts of the sensor or sensor assembly to a flexible substrate, such as a flex circuit. In one aspect, a flex circuit with corresponding contact portions electrically couples the sensor to a controller via the sensor contact pads.

In one aspect, the electrochemical analyte sensor assembly may be configured for an intravenous insertion to a vascular system of a subject. In order to accommodate the sensor within the confined space of a device suitable for intravenous insertion, the sensor assembly is assembled onto the flexible circuit.

Medical devices adaptable to the sensor assembly as described above include, but are not limited to a central venous catheter (CVC), a pulmonary artery catheter (PAC), a probe for insertion through a CVC or PAC or through a peripheral IV catheter, a peripherally inserted catheter (PICC), Swan-Ganz catheter, an introducer or an attachment to a Venous Arterial blood Management Protection (VAMP) system. Any size/type of Central Venous Catheter (CVC) or intravenous devices may be used or adapted for use with the sensor assembly.

For the foregoing discussion, the implementation of the sensor or sensor assembly is disclosed as being placed within a catheter, however, other devices as described above are envisaged and incorporated in aspects of the embodiments disclosed herein. The sensor assembly will preferably be applied to the catheter so as to be flush with the OD of the catheter tubing. This may be accomplished, for example, by thermally deforming the OD of the tubing to provide a recess for the sensor. The sensor assembly may be bonded in place, and sealed with an adhesive (e.g., urethane, 2-part epoxy, acrylic, etc.) that will resist bending/peeling, and adhere to the urethane CVC tubing, as well as the materials of the sensor. Small diameter electrical wires may be attached to the sensor assembly by soldering, resistance welding, or conductive epoxy. These wires may travel from the proximal end of the sensor, through one of the catheter lumens, and then to the proximal end of the catheter. At this point, the wires may be soldered to an electrical connector.

The sensor assembly as disclosed herein can be added to a catheter in a variety of ways. For example, an opening may be provided in the catheter body and a sensor or sensor assembly may be mounted inside the lumen at the opening so that the sensor would have direct blood contact. In one aspect, the sensor or sensor assembly may be positioned proximal to all the infusion ports of the catheter. In this configuration, the sensor would be prevented from or minimized in measuring otherwise detectable infusate concentration instead of the blood concentration of the analyte. Another aspect, an attachment method may be an indentation on the outside of the catheter body and to secure the sensor inside the indentation. This may have the added advantage of partially isolating the sensor from the temperature effects of any added infusate. Each end of the recess may have a skived opening to 1) secure the distal end of the sensor and 2) allow the lumen to carry the sensor wires to the connector at the proximal end of the catheter.

Preferably, the location of the sensor assembly in the catheter will be proximal (upstream) of any infusion ports to prevent or minimize IV solutions from affecting analyte measurements. In one aspect, the sensor assembly may be about 2.0 mm or more proximal to any of the infusion ports of the catheter.

In another aspect, the sensor assembly may be configured such that flushing of the catheter (e.g., saline solution) may be employed in order to allow the sensor assembly to be cleared of any material that may interfere with its function.

Sterilization of the Sensor or Sensor Assembly

Generally, the sensor or the sensor assembly as well as the device that the sensor is adapted to are sterilized before use. In one aspect, the fabrication process includes the sterilization of the sensor. Sterilization may be achieved using aseptic manufacturing, radiation (e.g., electron beam or gamma radiation), ethylene oxide or flash-UV sterilization, or other means know in the art.

Disposable portions, if any, of the sensor, sensor assembly or devices adapted to receive and contain the sensor preferably will be sterilized, for example using e-beam or gamma radiation or other know methods. The fully assembled device or any of the disposable components may be packaged inside a sealed container or pouch.

Central line catheters may be known in the art and typically used in the Intensive Care Unit (ICU)/Emergency Room of a hospital to deliver medications through one or more lumens of the catheter to the patient (different lumens for different medications). A central line catheter is typically connected to an infusion device (e.g., infusion pump, IV drip, or syringe port) on one end and the other end inserted in one of the main arteries or veins near the patient's heart to deliver the medications. The infusion device delivers medications, such as, but not limited to, saline, drugs, vitamins, medication, proteins, peptides, insulin, neural transmitters, or the like, as needed to the patient. In alternative embodiments, the central line catheter may be used in any body space or vessel such as intraperitoneal areas, lymph glands, the subcutaneous, the lungs, the digestive tract, or the like and may determine the analyte or therapy in body fluids other than blood. The central line catheter may be a double lumen catheter. In one aspect, an analyte sensor is built into one lumen of a central line catheter and is used for determining characteristic levels in the blood and/or bodily fluids of the user. However, it will be recognized that further embodiments may be used to determine the levels of other agents, characteristics or compositions, such as hormones, cholesterol, medications, concentrations, viral loads (e.g., HIV), or the like. Therefore, although aspects disclosed herein may be primarily described in the context of glucose sensors used in the treatment of diabetes/diabetic symptoms, the aspects disclosed may be applicable to a wide variety of patient treatment programs where a physiological characteristic is monitored in an ICU, including but not limited to blood gases, pH, temperature and other analytes of interest in the vascular system.

In another aspect, a method of intravenously measuring an analyte in a subject is provided. The method comprises providing a catheter comprising the sensor assembly as described herein and introducing the catheter into the vascular system of a subject. The method further comprises measuring an analyte of interest.

The above description discloses several methods and materials. These descriptions are susceptible to modifications in the methods and materials, as well as alterations in the fabrication methods and equipment. Such modifications will become apparent to those skilled in the art from a consideration of this disclosure or practice of the disclosure. Consequently, it is not intended that this disclosure be limited to the specific embodiments disclosed herein, but that it cover all modifications and alternatives coming within the true scope and spirit of the claims.

Referring now to the Figures, FIG. 1 is a schematic diagram of an exemplary electrochemical analyte sensor, and specifically, a basic amperometric analyte sensor. The depicted analyte sensor comprises two working electrodes: a first working electrode 12 and a second working electrode 14 (the second working electrode is sometimes referred to as the blank electrode). In some embodiments, the analyte sensor is a glucose sensor, in which case the first working electrode 12 may immobilize a glucose oxidase enzyme. The first working electrode 12 is typically an enzyme electrode either containing or immobilizing an enzyme membrane. The second working electrode 14 is typically identical in all respects to the first working electrode 12, except that it either does not contain an enzyme or contains an inactivated enzyme. The analyte sensor also includes a reference electrode 16 and a counter electrode 18. The reference electrode 16 establishes a fixed potential from which the potential of the working electrodes 12 and 14 are established. In order for the reference electrode 16 to function properly, no current must flow through it. The counter electrode 18 is used to conduct current in or out of the analyte sensor so as to balance the current generated by the working electrodes. The counter electrode 18 also provides a working area for conducting the majority of electrons produced from the oxidation chemistry back to the blood solution. Otherwise, excessive current may pass through the reference electrode 16 and reduce its service life. The four electrodes together are typically referred to as a cell. During operation, outputs from the working electrodes are monitored to determine the amount of an analyte of interest that is in the blood. Potentiometric analyte sensors operate in a similar manner to detect the amount of an analyte in a substance.

Figure 2:
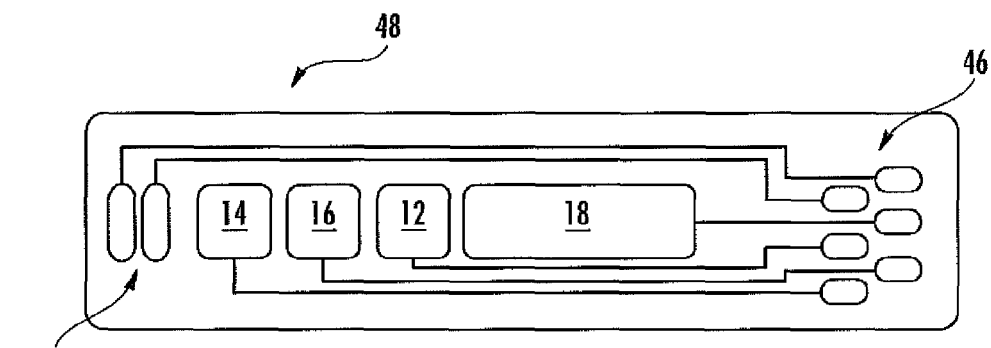
FIG. 2 is a schematic diagram of a top plan view of an electrochemical sensor component used in some aspects of the present invention.

FIG. 2 illustrates an exemplary electrochemical sensor component fabricated in accordance with aspects of the present invention. As illustrated, sensor 48 includes a first working electrode 12 and a second working (blank) electrode 14, a reference electrode 16, and a counter electrode 18. Each electrode is isolated in dielectric material and is connected to an isolated trace(s) leading to an isolated contact pad(s) 46. In this illustrated embodiment, the counter electrode 18 is dimensioned larger than the first and second working electrodes. The area of the counter electrode is generally made to be larger than the area of the working electrode such that the reaction on the counter electrode does not become a rate-determining step. In this illustrated embodiment, the working electrode is positioned between the counter electrode and reference electrode for optimization of the output signal. The sensor further comprises an isolated temperature sensor 40, which in this embodiment, is a thermistor comprising to electrodes 40a and 40b. The thermistor electrodes are also connected via traces to corresponding contact pads 46.

Figure 3:
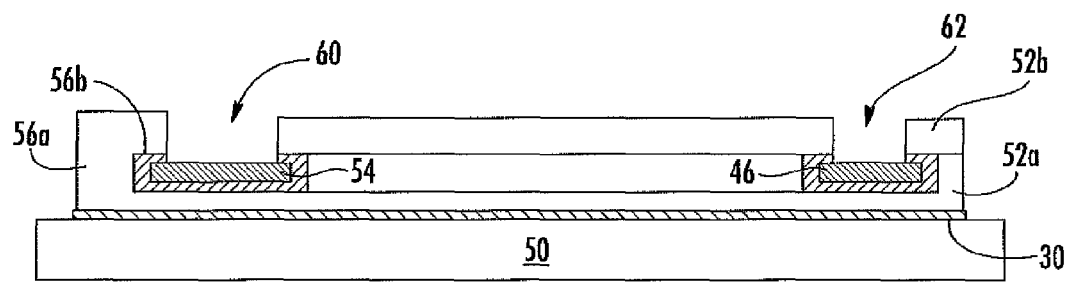
FIG. 3 is a schematic diagram of a cross-sectional view of a sensor used in some aspects of the present invention.

FIG. 3 illustrates the cross sectional view of an exemplary electrochemical sensor component fabricated in accordance with aspects of the present invention. As illustrated, the partially fabricated sensor includes opening 60 positioned over an isolated electrode 54 formed of conductive material sandwiched between first and second dielectric polymer layers 52a and 52b, respectively, and optionally, adhesive layers 56a and 56b and opening 62 positioned over a contact pad 46. Release layer 30 is positioned between the inorganic substrate 50 and the dielectric material layer to provide for lift-off of the sensor component after fabrication.

Figure 4:
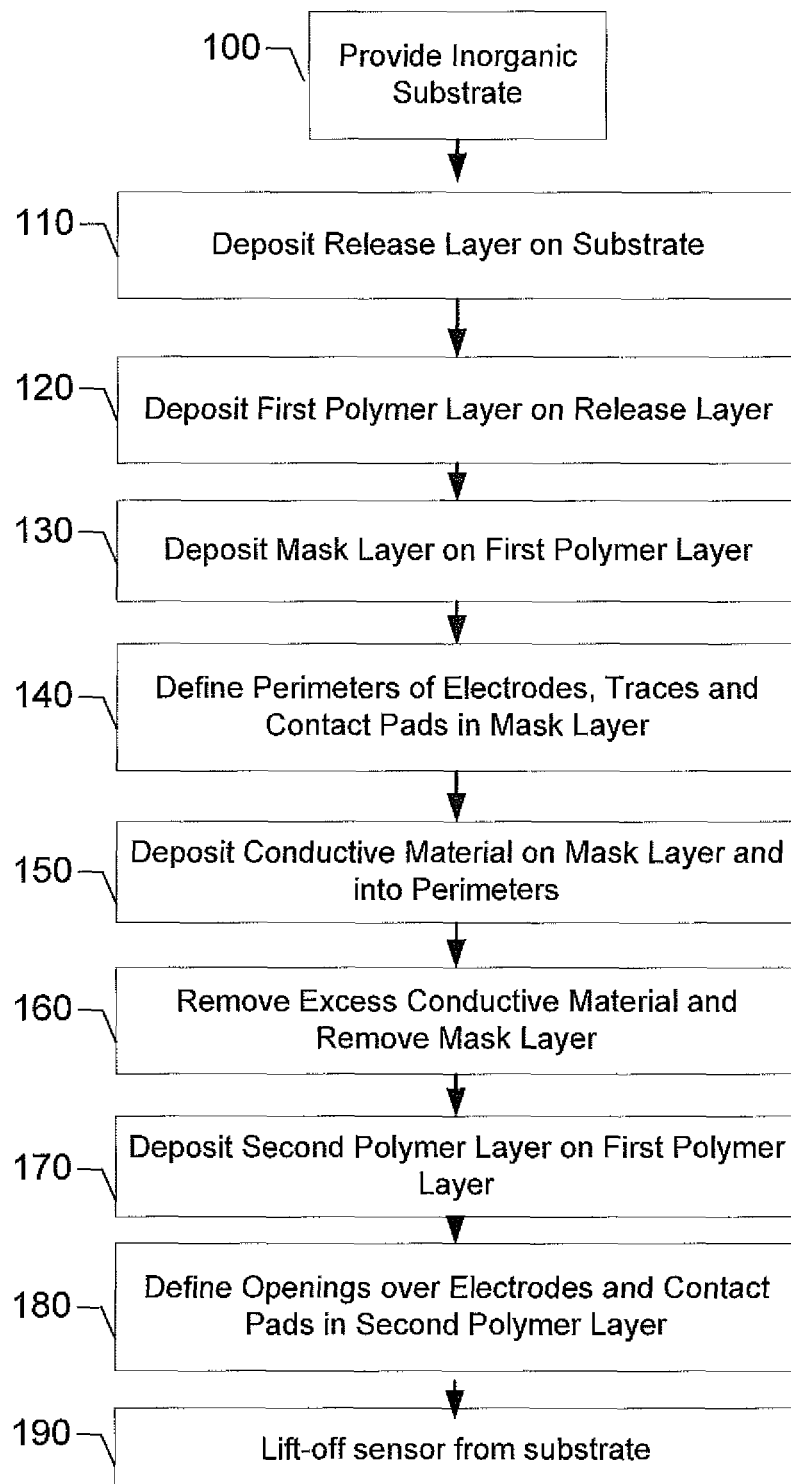
FIG. 4 is a flow chart of a method of fabricating an electrochemical sensor component used in a first embodiment of the present invention.
Figure 5:
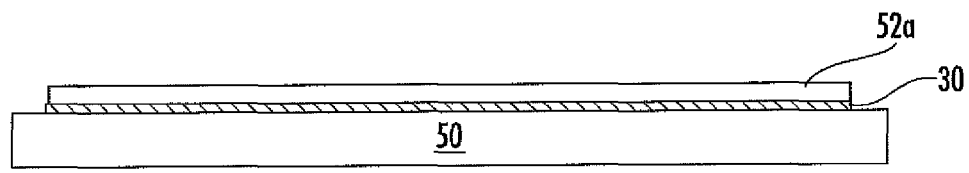
Figure 6A:
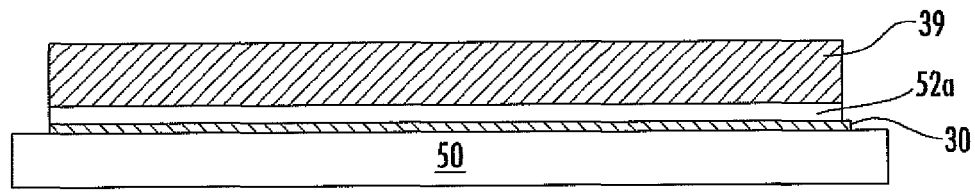
Figure 6B:
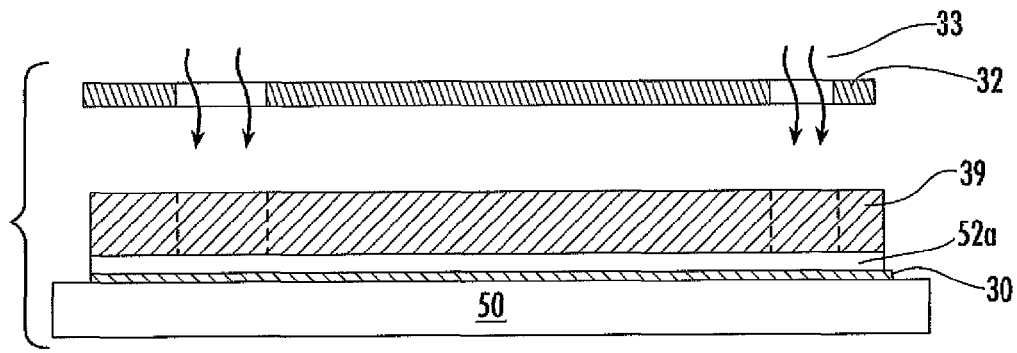
Figure 6C:
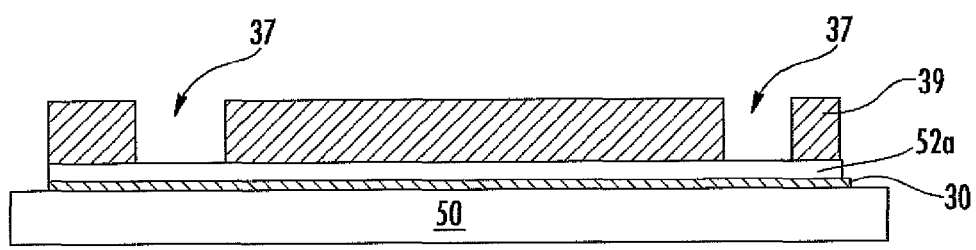
Figure 7:
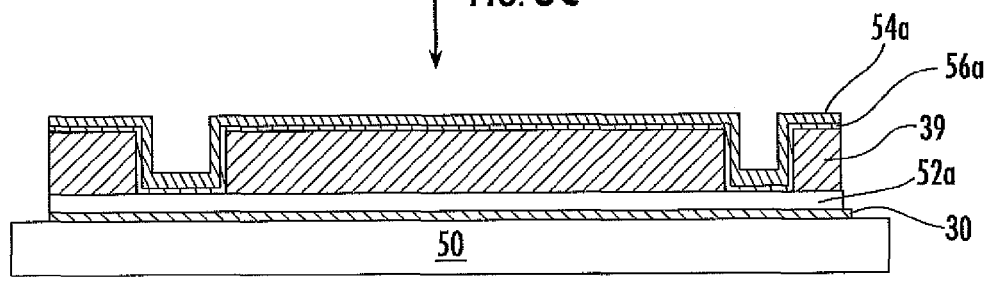

Referring to FIG. 4, a block diagram depicting a first embodiment of the sensor component fabrication corresponding to FIGS. 5-10 is provided. Thus, substrate 50 of semiconductor material, such as silicon is provided. (See block 100). Release layer 30 is deposited on the substrate (See block 110). A first dielectric polymer layer 52a is deposited on the release layer. (See block 120 and as shown in FIG. 5). A mask layer 39, such as a photoresist, is deposited on the first polymer coating, for example, by spin coating. (See block 130 and as shown in FIG. 6A). The mask layer is patterned/developed to provide perimeters for the deposition of the conductive material forming the electrodes and contact pads, as well as traces connecting the electrodes to the contact pads. (See block 140). Thus, as shown in FIG. 6B, actinic radiation 33 (e.g., x-ray, gamma, e-beam, DUV, UV, 1-line, G-line, etc.) is passed thru patterned reticule 32 exposing mask layer 39. Development of the exposed areas, which in this example is by way of a positive photoresist, provides perimeters 37, as shown in FIG. 6C. Conductive material 54a (and optionally adhesive layer 56a) is then deposited into the perimeters defining the electrodes, traces and contact pads, such as by chemical vapor deposition (CVD) or plating (electro- or electroless). (See block 150 and as shown in FIG. 7). Excess conductive material is removed (e.g., using chemical polishing, lift-off or etching techniques), along with the mask layer providing isolated features (electrodes 54, traces (not shown) and contact pads 46). (See block 160 and as shown in FIG. 8). Second dielectric layer 52b of photosensitive material (e.g., polyimide or polyepoxide) is deposited over isolated conductive features and on first flexible dielectric layer. (See block 170 and as shown in FIG. 9A). The second flexible dielectric layer is patterned/developed to provide openings 60 and 62 over the conductive electrode 54 and contact pad 46, respectively. (See block 180 and as shown in FIG. 9B and FIG. 9C). Lift-off of the sensor from the substrate is achieved via release layer 30, which provides for separation of the first polymer layer from the substrate resulting in an electrochemical sensor component. (See block 190 and as shown in FIG. 10). Sensing chemistry may be introduced into the openings over one or more of the working electrodes (not shown) at this point, or optionally, prior to release of the substrate.

In one aspect, the process as described with reference to FIGS. 4-10 is performed without the use of release layer 30 or the release of the first polymer layer 52a from substrate 50 (not shown). In this aspect, the fabricated sensors may be die-cut from the inorganic substrate using known MEMS/IC manufacturing techniques.

Figure 11:
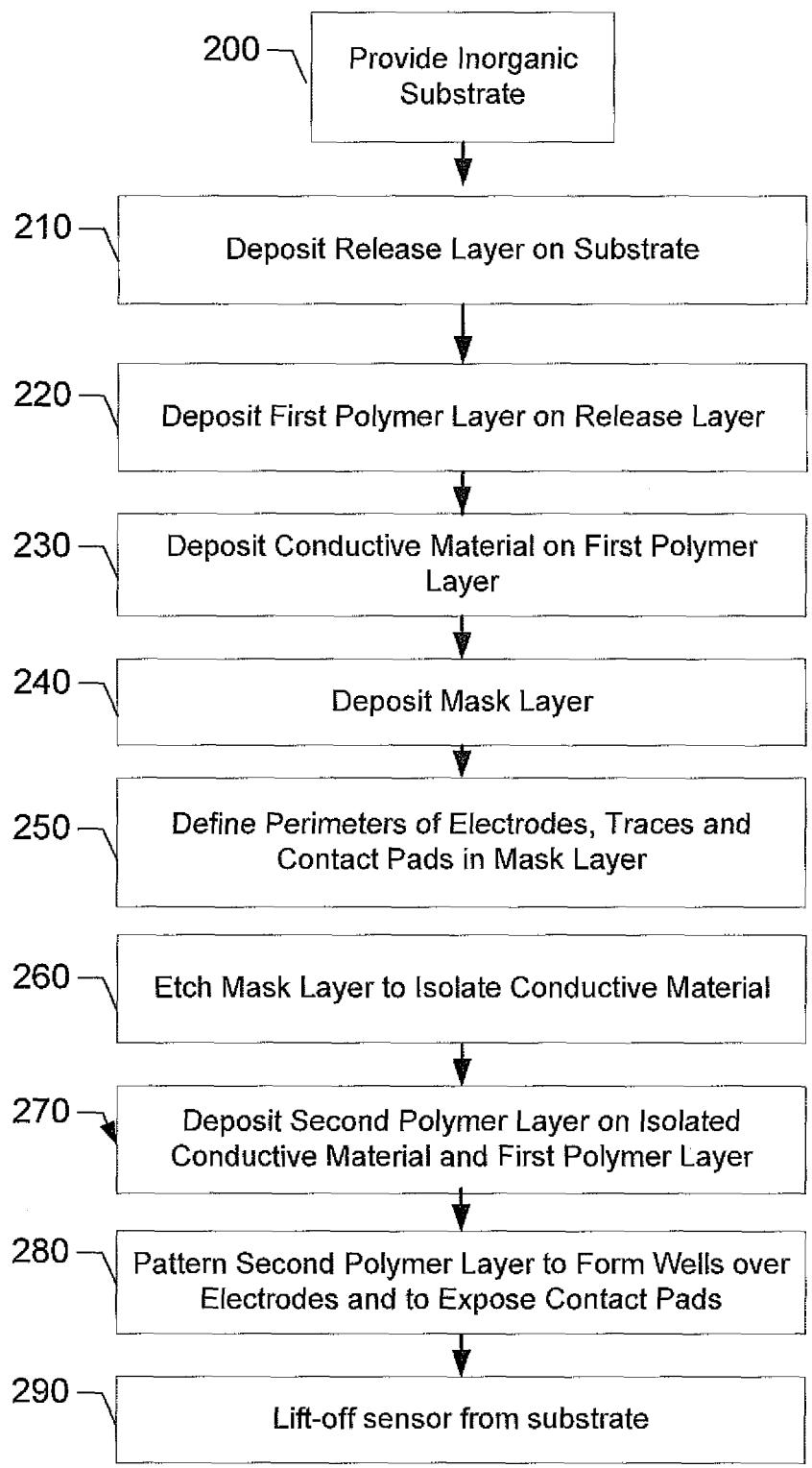
FIG. 11 is a flow chart of a method of fabricating an electrochemical sensor component used in a second embodiment of the present invention.
Figure 12:
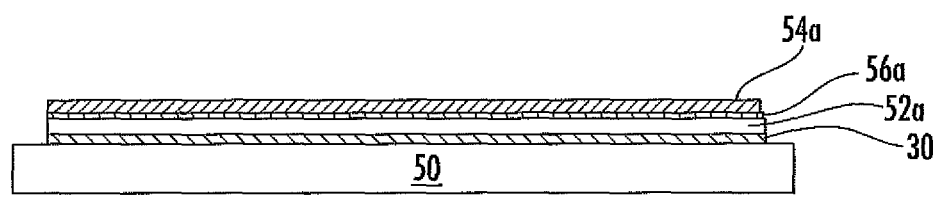
FIGS. 12-20 are schematic diagrams of a cross-sectional views illustrating the second embodiment of a fabrication process of an electrochemical sensor component.
Figure 13:
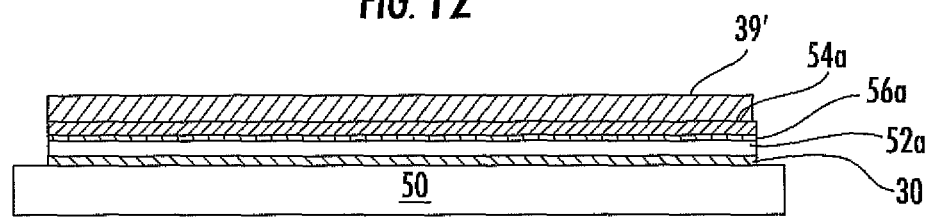
Figure 14:
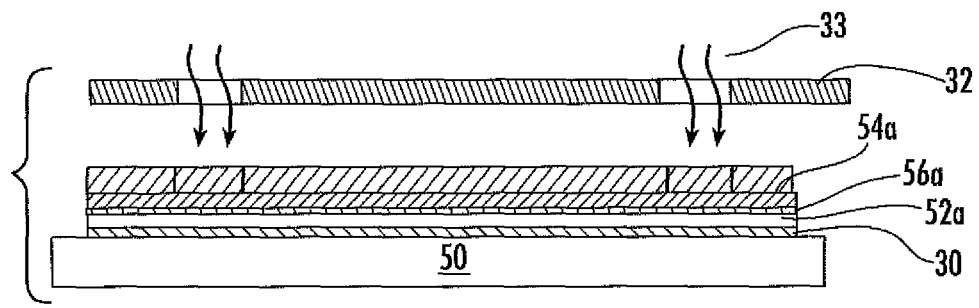
Figure 15:
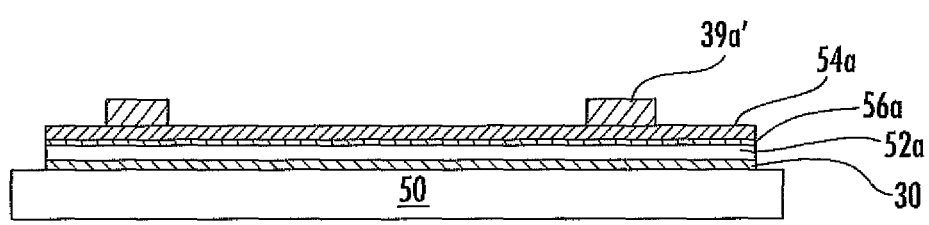
Figure 16:
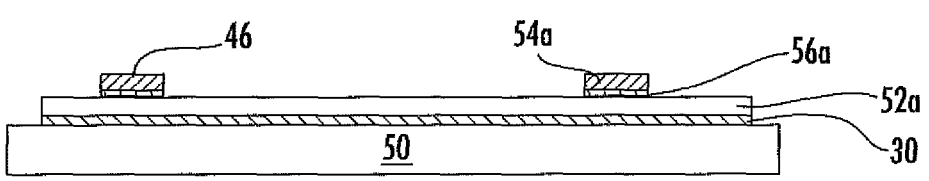
Figure 17:
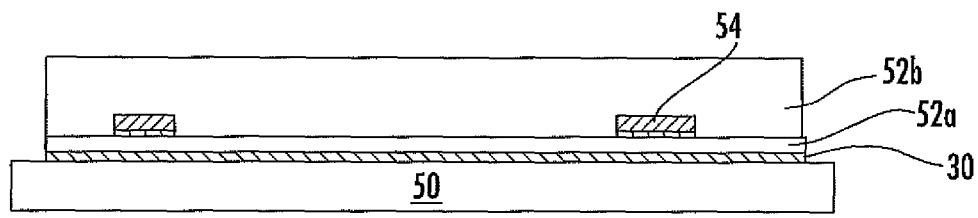
Figure 18:
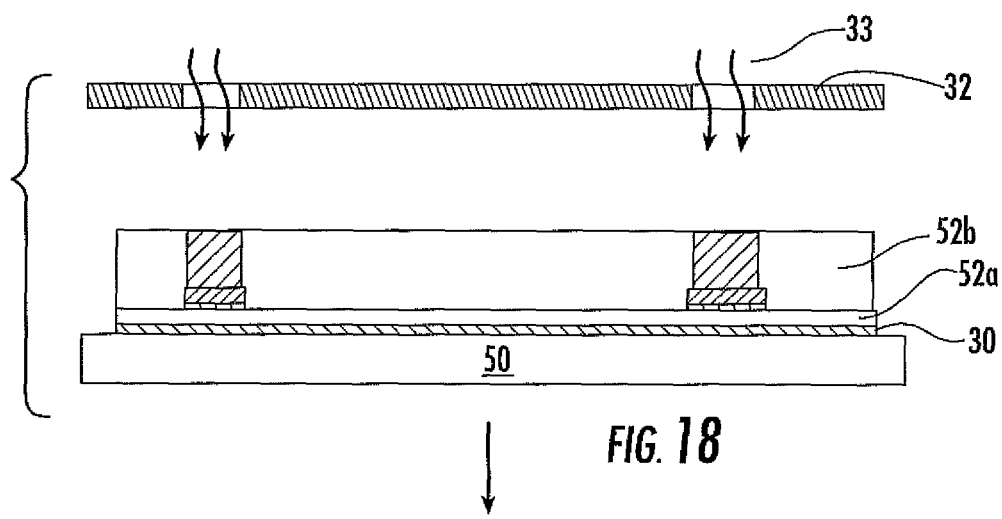
Figure 19:
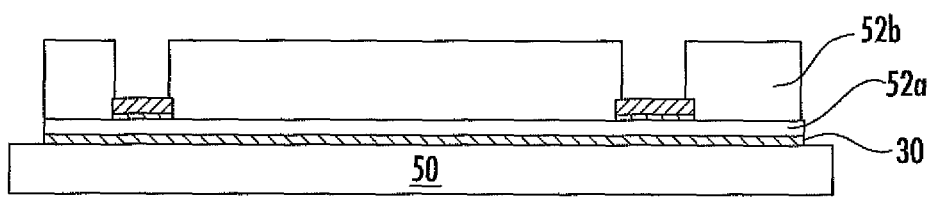
Figure 20:

Referring now to FIG. 11, a block diagram depicting a second embodiment of the sensor fabrication corresponding to FIGS. 12-20 is provided. Thus, substrate 50 of semiconductor material, such as silicon is provided. (See block 200). Release layer 30 is deposited on the substrate (See block 210). A first polymer layer 52a is then applied onto the release layer such as by coating or deposition. (See block 220). Conductive material 54a (and optionally adhesive layer 56a) is deposited on the first polymer layer. (See block 230 and as shown in FIG. 12). Mask layer 39 (over optional adhesion layer 56) is deposited over the conductive material 54. (See block 240 and as shown in FIG. 13). Perimeters 39a' for the conductive material are patterned into mask layer 39'. (See block 250 and as shown in FIGS. 14-15). Mask layer is etched along with excess conductive material to provided isolated (free standing) conductive electrodes (46, 54) on first polymer layer 52a. (See block 260 and as shown in FIG. 16). A second polymer layer 52b, such as a photosensitive dielectric material, is deposited on the isolated conductive material and first polymer coating, for example, by spin coating. (See block 270 and as shown in FIG. 17). The second polymer layer may be patterned/developed to provide openings over the electrodes and contact pads. (See block 280). Thus, as shown in FIG. 18, actinic radiation 33 (e.g., x-ray, gamma, e-beam, DUV, UV, I-line, G-line, etc.) is passed thru patterned reticule 32 exposing second dielectric layer 52b. Development of the exposed areas, which in this example is by way of a positive photoresist, provides openings 60 and 62, as shown in FIG. 19. The perimeters/openings may alternatively be formed using laser ablation techniques (with or without a reticule). Lift-off of the sensor from the substrate is achieved via release layer 30, which provides for separation of the first dielectric layer from the substrate resulting in an electrochemical sensor component. (See block 290 and as shown in FIG. 20). The sensing chemistry may be introduced into the openings over the working electrodes.

In one aspect, the process as described with reference to FIGS. 11-20 is performed without the use of release layer 30 or the release of the first dielectric layer 52a from substrate 50. In this aspect, the fabricated sensors may be individually separated from the inorganic substrate using known MEMS/IC manufacturing techniques, for example, die cutting or stamping.

Figure 21:
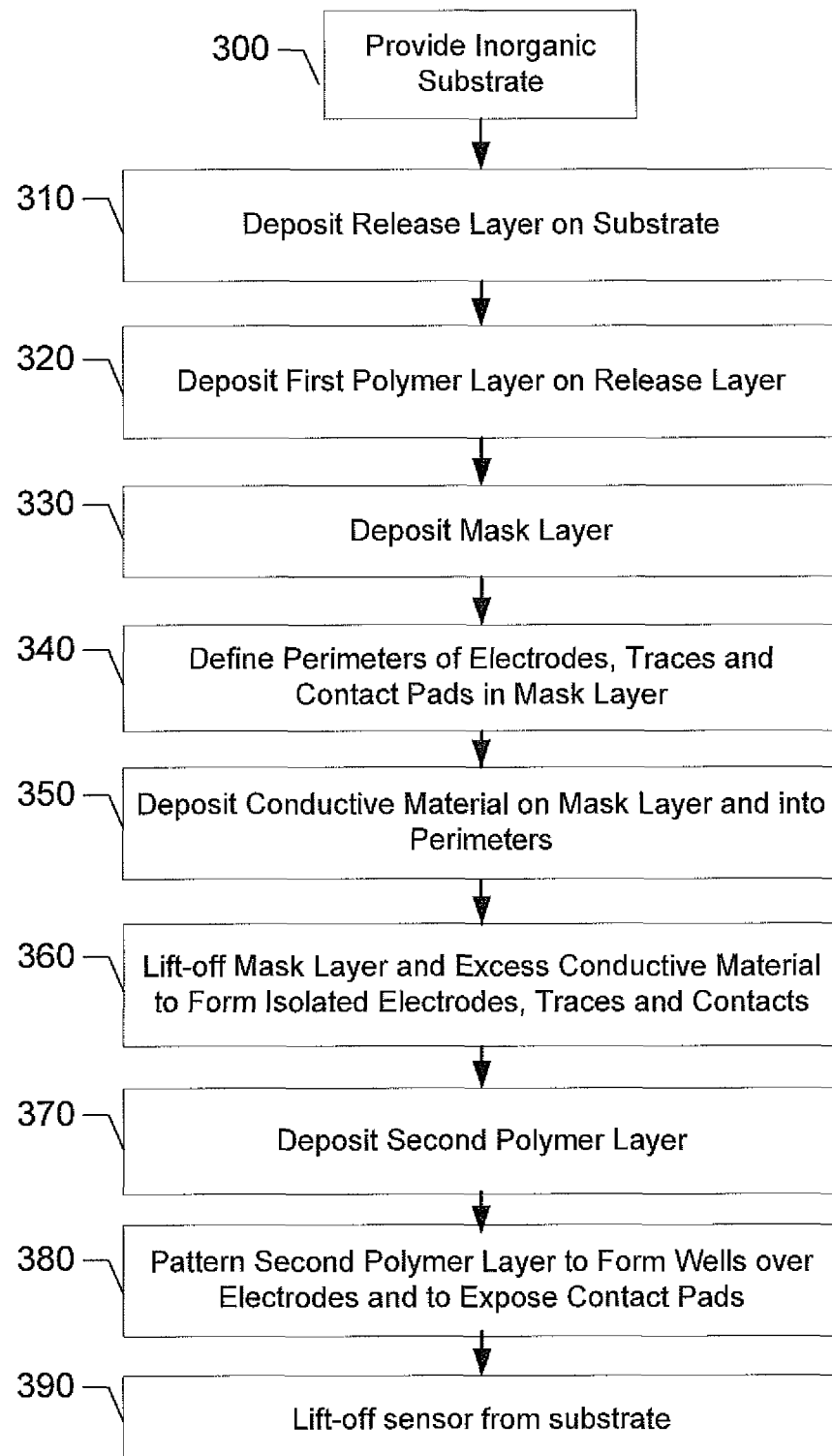
FIG. 21 is a flow chart of a method of fabricating an electrochemical sensor component used in a third embodiment of the present invention.
Figure 22:
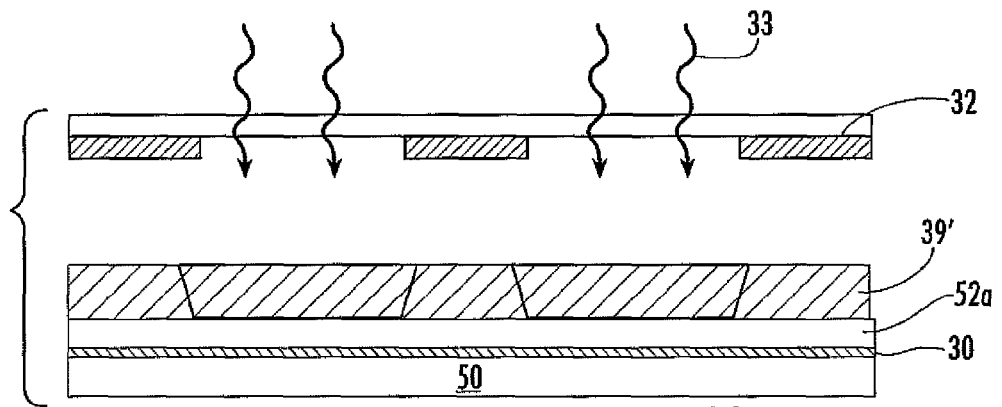
FIGS. 22-28 are schematic diagrams of a cross-sectional views illustrating the third as embodiment of a fabrication process of an electrochemical sensor component.
Figure 23:
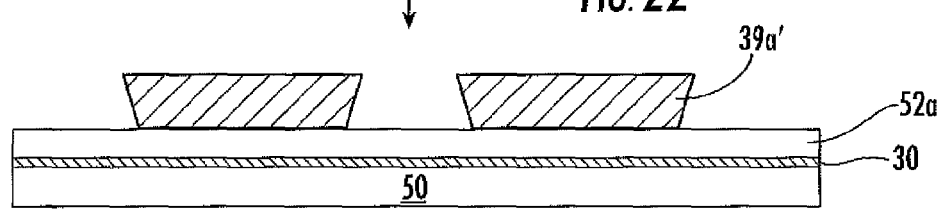
Figure 24:
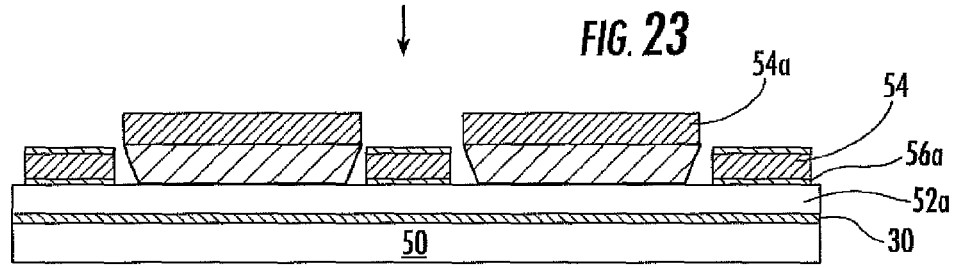
Figure 25:
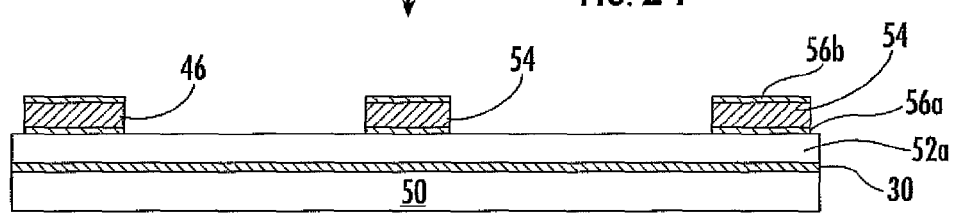
Figure 26:
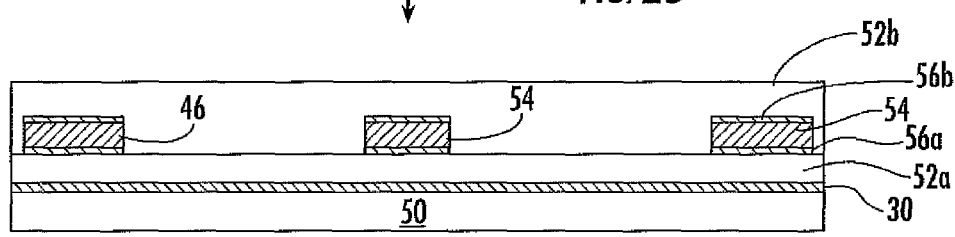
Figure 27A:
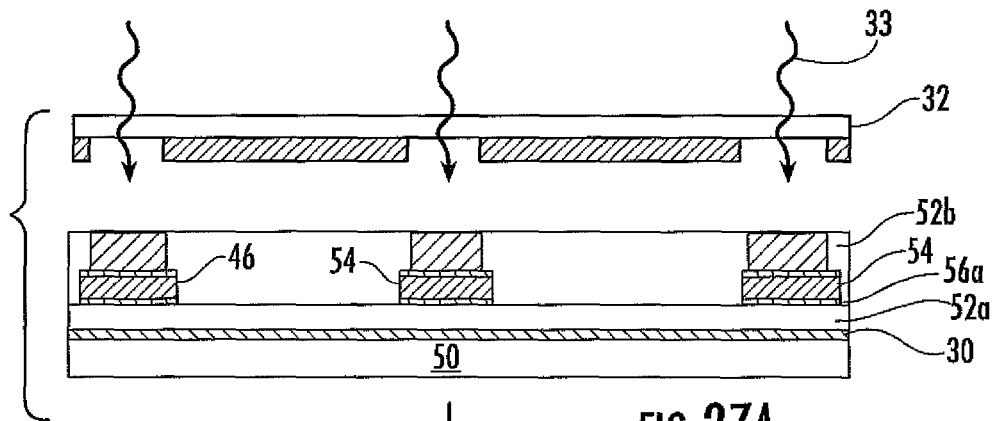
Figure 27B:
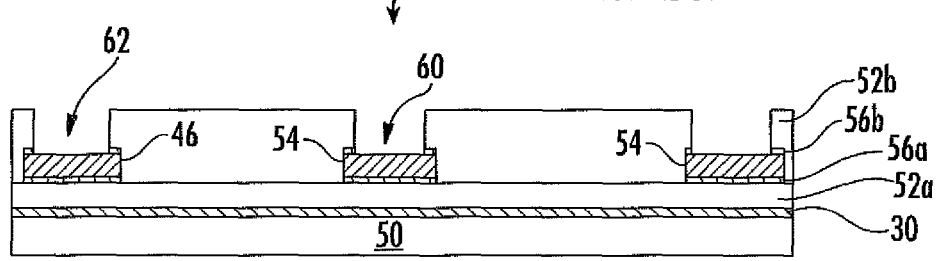
Figure 28:
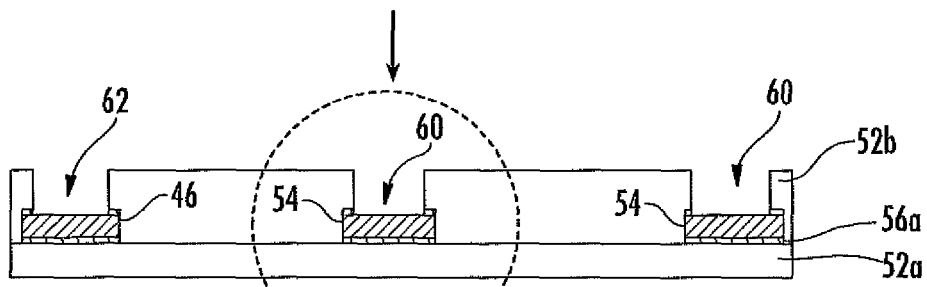

Referring now to FIG. 21, a block diagram depicting a third embodiment of the sensor fabrication corresponding to FIGS. 22-28 is provided. Thus, substrate 50 of semiconductor material, such as silicon is provided. (See block 300). Release layer 30 is deposited on the substrate (See block 310). First dielectric layer 52a is applied onto substrate 50, such as by spin coating. (See block 320). Photosensitive mask layer 39' is then applied onto the release layer such as by coating or deposition. (See block 330). The mask layer is patterned and developed to provide perimeters for the electrodes, traces and contact pads. (See block 340). Thus, as shown in FIG. 22, actinic radiation 33 (e.g., x-ray, gamma, e-beam, DUV, UV, 1-line, G-line, laser, etc.) is passed thru patterned reticule 32 exposing photosensitive mask layer 39'. Development of the un-exposed areas, which in this example is by way of negative photoresist mask layer 39', provides perimeters 37 between features 39a', as shown in FIG. 23. Optionally, a first adhesion layer 56a may be applied to the exposed first polymer layer. Conductive material 54a is deposited over mask layer 39' and into perimeters formed on the first dielectric layer. (See block 350 and as shown in FIG. 24). Using lift-off techniques, the mask layer and excess conductive material are removed to provide isolated (free standing) conductive structures (46, 54) on the first polymer layer 52a. (See block 360 and as shown in FIG. 25). A photosensitive second dielectric layer 52b (and optional second adhesion layer 56b) is deposited over the isolated conductive material and first polymer layer 52a. (See block 370 and as shown in FIG. 26). Exposure of photosensitive dielectric layer 52b to actinic radiation 33 and development provides openings 60 and 62 formed in the second dielectric layer 52b (and the optional second adhesion layer 56b) exposing portions of isolated conductive material 54. (See block 380 and as shown in FIGS. 27A-B). The perimeters/openings may alternatively be formed using laser ablation techniques (with or without a reticule). Lift-off of the sensor from the substrate is achieved via release layer 30, which provides for separation of the first polymer layer from the substrate resulting in an electrochemical sensor component. (See block 390 and as shown in FIG. 28). The sensing chemistry may be introduced into the openings over one or more of the working electrodes as will now be described.

Figure 29:
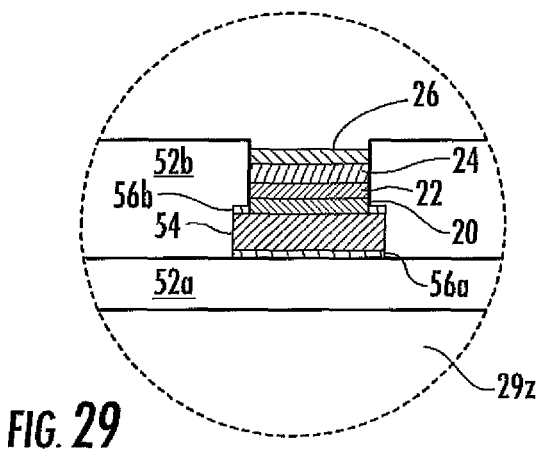
FIG. 29 is a schematic diagram of an exploded cross-sectional views illustrating an analyte sensing membrane.

FIG. 29 is an exploded cross-sectional view of an exemplary well positioned over an electrode (e.g., a working electrode) of FIG. 28. Depending on the functionality of the electrode, an analyte sensing membrane is then applied to the exposed electrode in the well. For example, as shown in exploded view 29z, if the electrode is a working electrode, the analyte sensing membrane may be applied comprising: a hydrophilic layer 20; an interference layer 22; an enzyme layer 24; and a flux-limiting layer 26, each of the layers of the analyte sensing membrane (and optional additional layers such as a bioactive layer) having been described above. Methods of depositing the layers of the analyte sensing membrane include, for example, (micro)pipetting, casting, dip-coating, (micro)spray-coating, ink-jet spray coating, vapor coating and the like.

Figure 30:
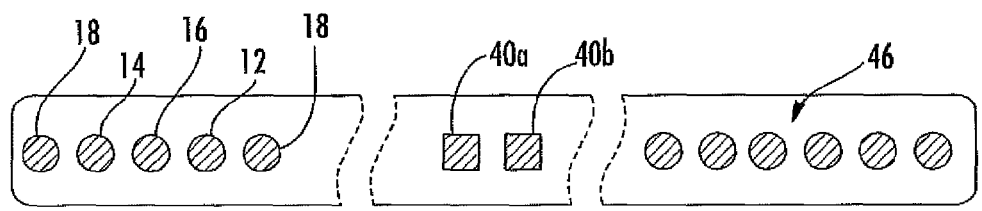
FIGS. 30-32 are schematic diagrams of a top plan views of sensor electrode, trace and contact pad fabrication used in some aspects of the present invention.
Figure 31:
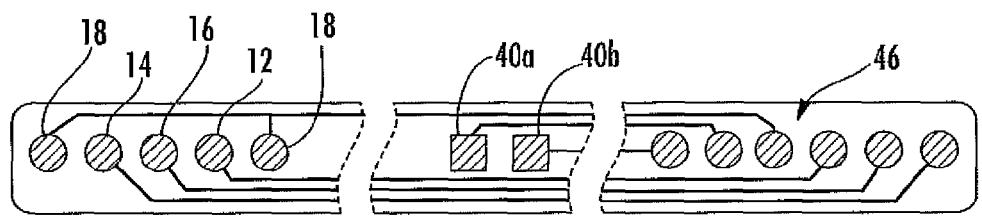
Figure 32:
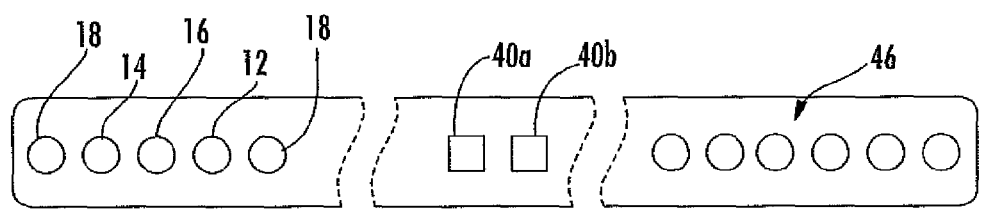
Figure 33:
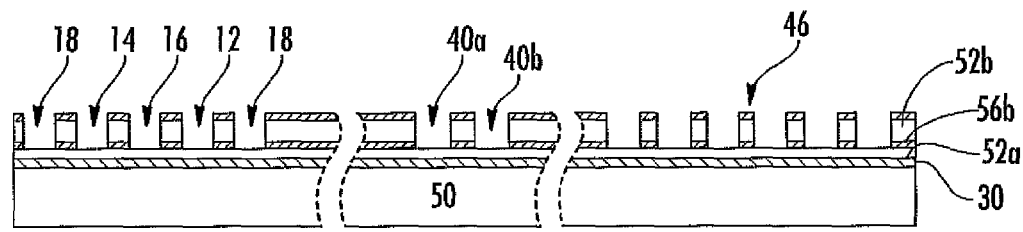
FIG. 33 is a schematic diagram of a cross-sectional view illustrating the sensor of FIG. 32.

FIGS. 30-32 illustrate detailed views of sample sensor 70 architecture similar to the sensor architecture of FIG. 6A. Thus, top plan views of an exemplary fabrication process steps are described herein. FIG. 30 depicts the top plan view of isolated conductive features comprising first working electrode 12 and second working (blank) electrodes 14, reference electrode 16, counter electrode 18 and contact pads 46. Also provided are electrodes, 40a, 40b, for the temperature sensor. FIG. 31 illustrates electrical connection via traces between the contact pads and the electrodes. FIG. 32 depicts the top plan view of the isolated openings positioned over the electrodes contact pads 46 and thermistor 40a, 40b. FIG. 33 is a cross-sectional view of the openings of the sensor depicted in FIG. 32. Contact pads 46 are also illustrated. It is noted that FIGS. 30-32 illustrate only the electrodes, traces, and contact pads of the sensor. Membrane layers over the various electrodes are not illustrated.

Figure 34:
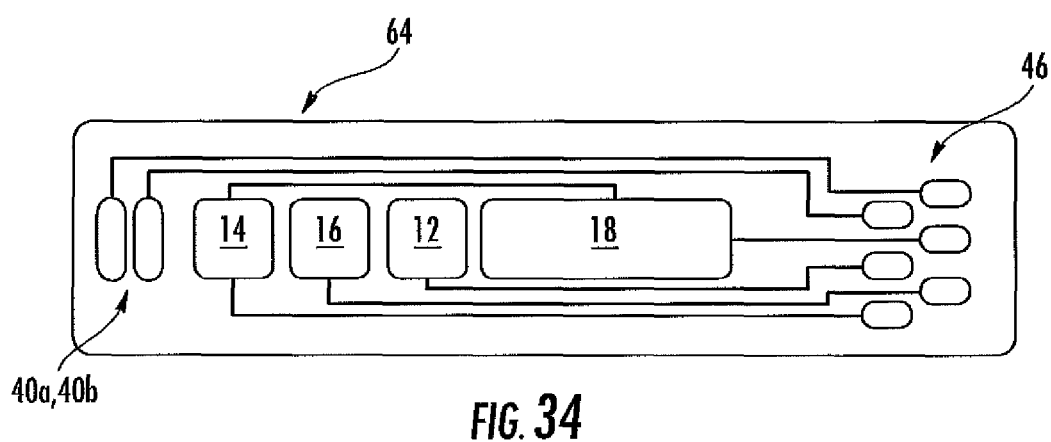
FIGS. 34-36 are schematic diagrams of a top plan views of sensor electrode, trace and contact pad configurations used in some aspects of the present invention.
Figure 35:
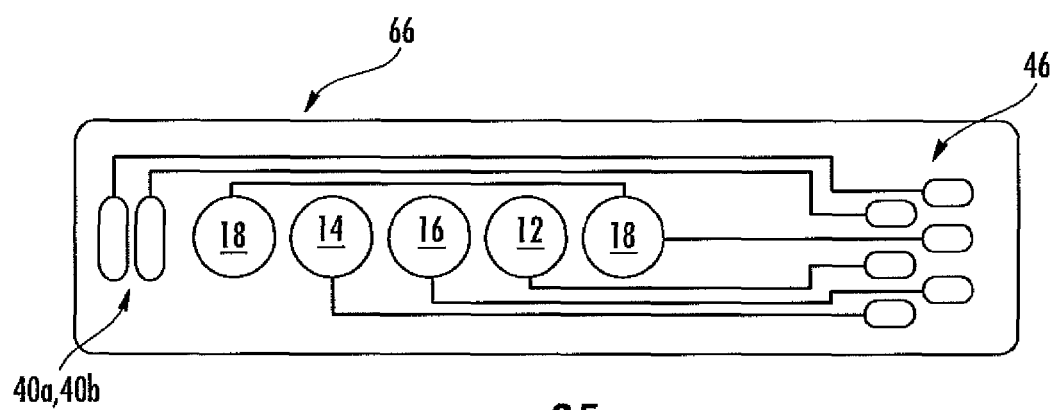
Figure 36:
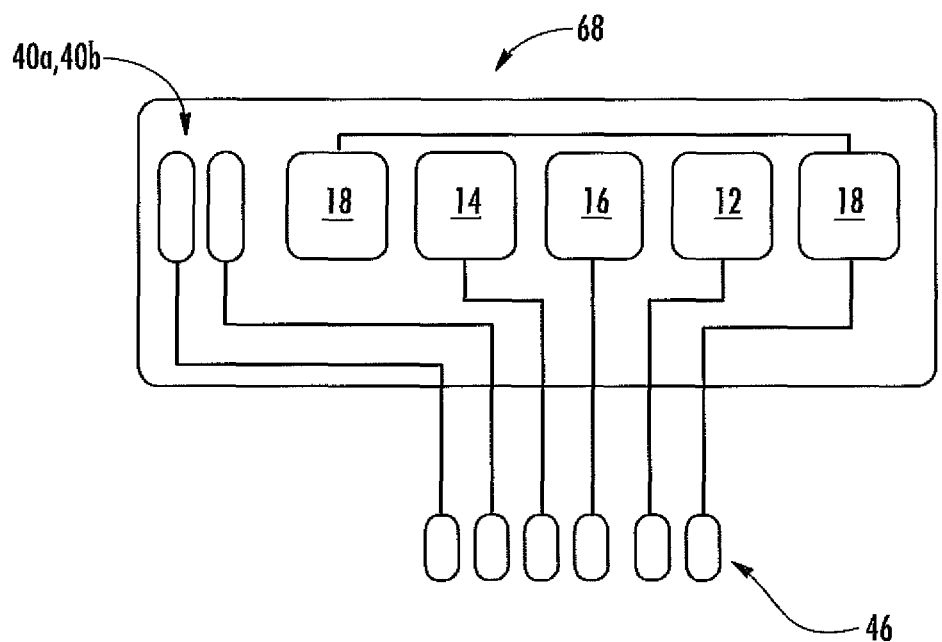
Figure 37:
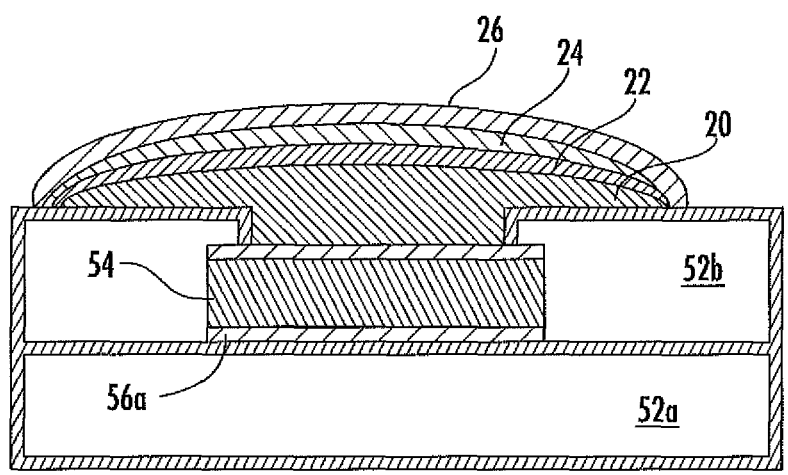
FIG. 37 is a schematic diagram of an analyte sensing membrane, whereby the individual layers of the analyte sensing membrane are draped over the opening exposing the working electrode, as used in some aspects of the present invention.

Referring now to FIGS. 34-36, illustrated are different structural/geometrical embodiments of the sensor structure. Other designs and layouts may be used. Thus, two smaller counter electrodes 18 are depicted in sensors 64, 66 and 68, as opposed to the larger single counter electrode as depicted in FIG. 2, while maintaining a larger surface area ratio between the counter electrode and working electrode. These sensor structures may be fabricated using the techniques described above. FIG. 37 represents an aspect of the analyte sensing membrane whereby the individual layers of the membrane are draped over the opening. In one aspect, (not shown) some or one of the layers (e.g., the flux-limiting layer) may be draped over the opening and underlying layers and/or may encapsulate the analyte sensing membrane to the dielectric layer.

A thin-film sensor component was fabricated by micromachining/IC processing on a silicon wafer substrate having an architecture similar to that depicted in FIG. 35 except no temperature electrodes were employed. Thus, silicon oxide (500 nm thickness) was sputtered as a release layer on a silicon wafer. A 10 μm layer of first dielectric material (polyimide precursor PI-2611, HD Microsystems) was applied on top of the silicon oxide by spin-coating and cured at 300° C. for 40 minutes in a nitrogen atmosphere. Layers of titanium (~500 Å)-platinum (~500 nm)-titanium (~500 Å) were sputtered sequentially and patterned for metal electrodes, pads and conductive traces. The titanium layers enhanced the adhesion between the polyimide and the platinum layer. A second dielectric layer of polyimide (5 μm thickness) was spin-coated and cured on the patterned metal layers. Silicon oxide (~500 nm thickness) etch stop was sputtered onto the polyimide and patterned using a photoresist layer to define openings for electrodes, contact pads and sensor outline. Etching of the second dielectric layer with patterned $SiO_2$ etch stop with oxygen-plasma RIE provided openings exposing the electrodes and contact pads. Finally, the sensor structure was released from silicon wafer by wet etching in HF solution (20% HF in 80% DI water). A thin-layer of silver (Ag) was electroplated on the reference electrode 16. Silver was then converted to silver/silver chloride (Ag/AgCl) electrochemically. There was no iron chloride or silver nitrate applied to the reference electrodes. As an initial step, hydrogen peroxide activity was evaluated on the electrodes prior to application of the analyte sensing membrane. An analyte sensing membrane was deposited comprising CAB/GOx-PVP layers to a working electrode. An EVA layer was spray applied using 4 passes of a 2 wt % EVA solution in xylene to encapsulate the analyte sensing membrane to the dielectric layer.

Figure 38:
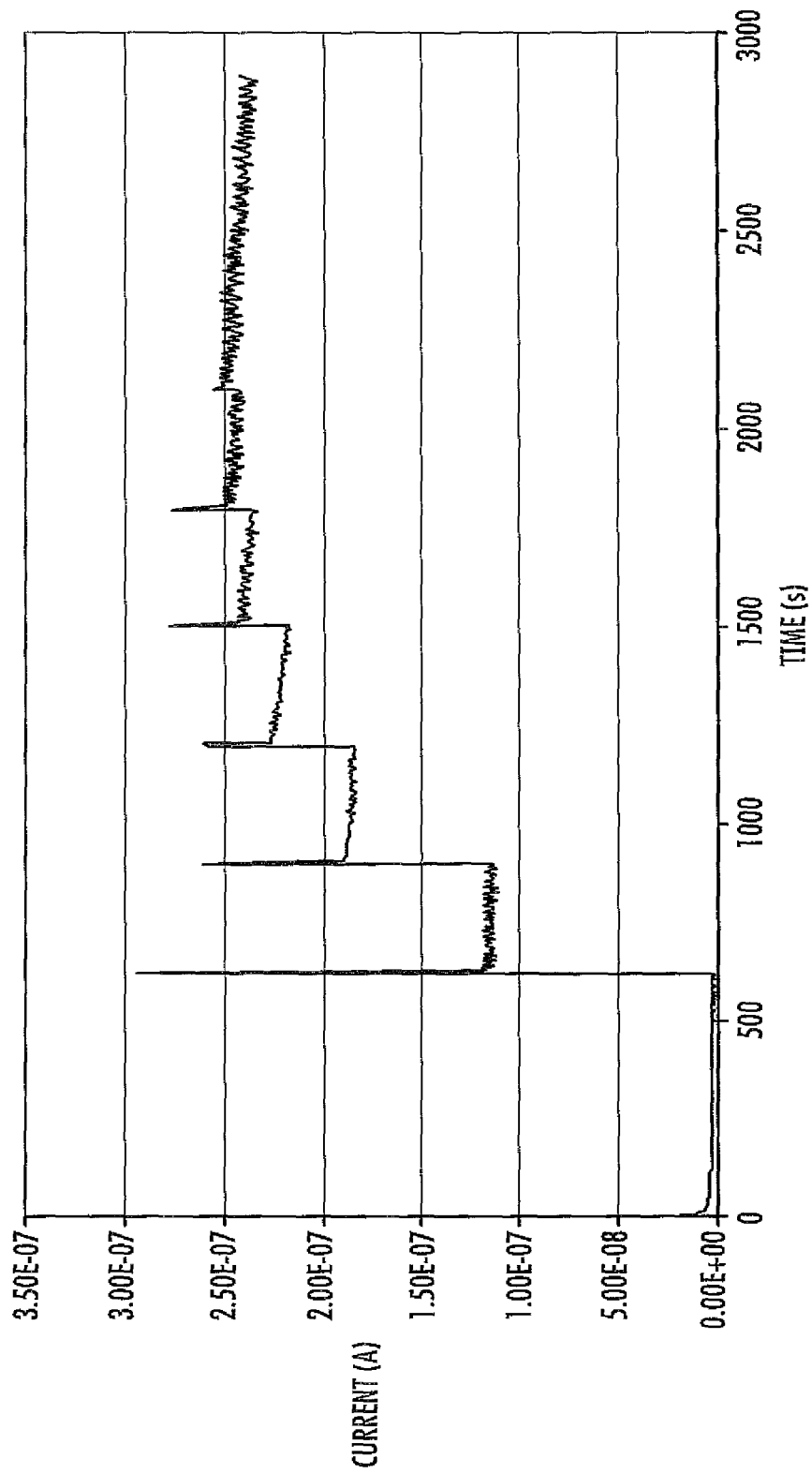
FIG. 38 is a chart of the current verses time of an experimental sensor used in an aspect of the present invention after exposure to concentrations of glucose.

As illustrated in FIG. 38, the sensor responded well for determining glucose concentration levels of a solution. FIG. 38 illustrates current outputs from the sensors at different glucose concentration levels using a working potential of 650 mV. Each step response is a result of dosing 50 mg/dL increments of glucose in PBS. The sensors showed good response to changes in glucose concentration. Although output drift was noted, such drift is likely due to over saturation of enzyme layer with glucose and/or drift in the reference electrodes.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification may be to be understood as being modified in all instances by the term "about." Accordingly, unless indicated to the contrary, the numerical parameters set forth herein may be approximations that may vary depending upon the desired properties sought to be obtained. At the very least, each numerical parameter should be construed in light of the number of significant digits and ordinary rounding approaches.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Therefore, it is to be understood that, within the scope of the appended claims, the invention may be practiced other than as specifically described herein.

That which is claimed:

1. A method for fabricating a flexible electrochemical sensor component comprising:
   providing a substrate;
   depositing a release layer on substantially all the substrate;

depositing a first flexible dielectric layer on substantially all of the release layer;

forming a plurality of individual continuously connected electrodes, traces and contact pads comprised of a conductive material over the first flexible dielectric layer;

depositing a second flexible dielectric layer over the first flexible dielectric layer and the plurality of individual continuously connected electrodes, traces and contact pads;

forming openings in the second flexible dielectric layer exposing at least a portion of at least one of the individual continuously connected electrodes and contact pads; and removing the release layer between the first flexible dielectric material and the substrate, whereby the flexible electrochemical sensor component is released from the substrate.

2. The method of claim 1, wherein the release layer comprises at least one of (i) a material having a solubility in a solvent that does not substantially dissolve the first or second flexible dielectric layers; (ii) a material having an etch rate (wet or dry) faster than that of the first flexible dielectric layer; or (iii) a pressure sensitive adhesive material interposed between the first dielectric material and the substrate.

3. The method of claim 1, wherein the release layer is silicon dioxide, silica glass, or aluminum.

4. The method of claim 1, wherein the release layer is chemically removed.

5. The method of claim 1, further comprising depositing a first adhesion layer between at least a portion of the first flexible dielectric material and the conductive material and depositing a second adhesion layer between the conductive material and at least a portion of the second flexible dielectric material.

6. The method of claim 1, further comprising depositing an analyte sensing membrane in the opening positioned over the electrode.

7. The method of claim 6, wherein the analyte sensing membrane comprises:
a hydrophilic polymer layer;
an interference layer;
an enzyme layer; and
a flux-limiting layer.

8. The method of claim 6, wherein the analyte sensing membrane encapsulates the opening over the electrode.

* * * * *